US012358853B2

(12) United States Patent
Minoux et al.

(10) Patent No.: US 12,358,853 B2
(45) Date of Patent: Jul. 15, 2025

(54) ELECTRIFIED PROCESS TO CONDUCT TRANSFORMATION OF ALCOHOLS INTO CORRESPONDING OLEFINS IN A FLUIDIZED BED REACTOR

(71) Applicant: TOTALENERGIES ONETECH, Courbevoie (FR)

(72) Inventors: Delphine Minoux, Seneffe (BE); Walter Vermeiren, Seneffe (BE); Gleb Veryasov, Seneffe (BE)

(73) Assignee: TOTALENERGIES ONETECH, Courbevoie (FR)

( * ) Notice: Subject to any disclaimer, the term of this patent is extended or adjusted under 35 U.S.C. 154(b) by 0 days.

(21) Appl. No.: 18/832,785

(22) PCT Filed: Jan. 3, 2023

(86) PCT No.: PCT/EP2023/050067
§ 371 (c)(1),
(2) Date: Jul. 24, 2024

(87) PCT Pub. No.: WO2023/143877
PCT Pub. Date: Aug. 3, 2023

(65) Prior Publication Data
US 2025/0136528 A1    May 1, 2025

(30) Foreign Application Priority Data

Jan. 25, 2022 (EP) .................................... 22315020

(51) Int. Cl.
*C07C 1/24* (2006.01)
*B01J 8/42* (2006.01)
*B01J 19/08* (2006.01)

(52) U.S. Cl.
CPC .................. *C07C 1/24* (2013.01); *B01J 8/42* (2013.01); *B01J 19/087* (2013.01); *B01J 2208/00407* (2013.01); *B01J 2219/0809* (2013.01)

(58) Field of Classification Search
CPC ... C07C 1/24; C07C 11/02; B01J 19/08; B01J 29/00; B01J 19/00; B01J 29/06
See application file for complete search history.

(56) References Cited

U.S. PATENT DOCUMENTS 11,964,934 B2 * 4/2024 Veryasov ............... C10G 11/18

FOREIGN PATENT DOCUMENTS

EP        2883604 A1    6/2015
WO    2019/145279 A1    8/2019

OTHER PUBLICATIONS

Search Report dated Mar. 30, 2023 issued in corresponding International Application No. PCT/EP2023/050067.
(Continued)

*Primary Examiner* — Sharon Pregler
(74) *Attorney, Agent, or Firm* — Nath, Goldberg & Meyer; Joshua B. Goldberg

(57) ABSTRACT

The disclosure concerns a process to perform a catalytic dehydration of alcohols having at least two carbon atoms into olefins, said process comprising the steps of a) providing one fluidized bed reactor and a bed comprising particles; b) putting the particles in a fluidized state to obtain a fluidized bed; c) heating the fluidized bed to a temperature ranging from 200° C. to 500° C.; remarkable in that the particles of the bed comprise electrically conductive particles and particles of one or more solid acid catalysts, wherein at least 10 wt. % of the particles based on the total weight of the particles of the bed are electrically conductive particles and have a resistivity ranging from 0.001 Ohm·cm to 500 Ohm·cm at 400° C.; and in that the step c) of heating
(Continued)

the fluidized bed is performed by passing an electric current through the fluidized bed.

17 Claims, 3 Drawing Sheets

(56) References Cited

OTHER PUBLICATIONS

Written Opinion dated Mar. 30, 2023 issued in corresponding International Application No. PCT/EP2023/050067.

* cited by examiner

ELECTRIFIED PROCESS TO CONDUCT TRANSFORMATION OF ALCOHOLS INTO CORRESPONDING OLEFINS IN A FLUIDIZED BED REACTOR

This is a National Phase Application filed under 35 U.S.C. 371 as a national stage of PCT/EP2023/050067, filed Jan. 3, 2023, an application claiming the benefit of European Application No. 22315020.2, filed Jan. 25, 2022, the content of each of which is hereby incorporated by reference in its entirety.

FIELD OF THE DISCLOSURE

The present disclosure relates to a process for performing a catalytic dehydration of alcohols having at least two carbon atoms into corresponding olefins in a fluidized bed reactor wherein the reaction is performed without the need of an external heating device in the said fluidized bed reactor. The present disclosure aims to contribute to the replacement of the use of fossil carbon-based fuels heating devices. The present disclosure relates to the electrification of the chemical industry.

TECHNICAL BACKGROUND

Climate change and ongoing energy transition make it mandatory to replace fossil carbon-based fuels in chemical production and recycled processes with a more environmentally friendly decarbonized source of energy. In that context, alcohols appear as promising platform molecules: indeed, dehydration into corresponding olefins leads to the same monomers than those obtained via conventional petroleum routes while resulting in the same time to lower carbon emissions. Therefore, the conversion of alcohols into olefins therefore appears as a key process to contribute to carbon neutrality.

Among the technologies claimed to convert alcohols into olefins, most of them consider the use of conventional fixed bed reactors. A fluidized-bed process to dehydrate ethanol is described in U.S. Pat. No. 4,134,926 but does not avoid neither the use of burners, ovens or any other conventional heating means, and subsequently contributes to greenhouse gas emissions.

The present disclosure aims to provide a large-scale solution to one or more of the problems encountered in the prior art that is suitable for application in the industry, such as the chemical industry. The present disclosure aims to contribute to the replacement of the use of fossil carbon-based fuels heating devices in fluidized bed reactors. The present disclosure provides a solution to conduct a catalytic dehydration of alcohols into olefins using electricity as a sole source of energy.

SUMMARY OF THE DISCLOSURE

According to a first aspect, the disclosure provides for a process to perform a catalytic dehydration of one or more alcohols having at least two carbon atoms into one or more olefins, said process comprising the steps of:
  a) providing at least one fluidized bed reactor comprising at least two electrodes and a bed comprising particles;
  b) putting the particles of the bed in a fluidized state by passing upwardly through the said bed a fluid stream, to obtain a fluidized bed; and
  c) heating the fluidized bed to a temperature ranging from 200° C. to 500° C. to conduct the catalytic dehydration of an alcohol-containing feedstock into one or more olefins, wherein the alcohol-containing feedstock comprises one or more alcohols having at least two carbon atoms;

the process is remarkable in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm·cm to 500 Ohm·cm at 400° C.; wherein the catalytic composition comprises one or more solid acid catalysts; in that the step c) of heating the fluidized bed is performed by passing an electric current through the fluidized bed.

Surprisingly, it has been found that the use of electrically conductive particles, such as silicon carbide and/or graphite, in one or more fluidized bed reactors which are electrified, allows maintaining a temperature sufficient to carry out a catalytic dehydration of one or more alcohols having at least two carbon atoms into one or more olefins having the same number of carbons as the alcohol, requesting conditions such as temperature reaction ranging from 200° C. to 500° C. without the need of any external heating device. The use of at least 10 wt. % of electrically conductive particles within the particles of the bed allows minimizing the loss of heat when a voltage is applied. Thanks to the Joule effect, most, if not all, the electrical energy is transformed into heat that is used for the heating of the reactor medium.

For example, the electrically conductive particles are or comprise one or more selected from one or more metallic alloys, one or more non-metallic resistors, one or more metallic carbides, one or more metallic nitrides, one or more metallic phosphides, one or more carbon-containing particles, one or more superionic conductors, one or more phosphate electrolytes and/or any mixture thereof.

In preferred embodiment, the electrically conductive particles are or comprise one or more selected from one or more metallic alloys, one or more non-metallic resistors, one or more metallic carbides, one or more metallic nitrides, one or more metallic phosphides, one or more carbon-containing particles, one or more superionic conductors, and any mixture thereof.

Advantageously, said process further comprises a step (d) of recovering one or more olefins. Step (d) is performed after step (c).

In an embodiment, said step (d) is carried out and said process further comprises a step (e) of oligomerizing the one or more olefins recovered at step (d).

In an alternative embodiment, said step (d) is carried out and said process further comprises a step (f) of providing one or more aromatic compounds and a step (g) of alkylating said one or more aromatic compounds with the one or more olefins recovered at step (d).

In another alternative embodiment, said step (d) is carried out, and said process comprises a step (e) of oligomerizing one part of the one or more olefins recovered at step (d), said process further comprises a step (f) of providing one or more aromatic compounds and a step (g) of alkylating said one or more aromatic compounds with another part of the one or more olefins recovered at step (d), said step (g) being carried out concomitantly with said step (e). Whichever the embodiment chosen, said process further comprises the optional step (h) of hydrogenating the olefins after that step (e) and/or (g) has been carried out.

The oligomerization step (e) and/or the alkylation step (g) on the aromatic compounds provided upon step (f) and optionally the hydrogenation step (h) are carried out after the step (d) of recovering the one or more olefins, allowing to produce jet-fuel and to decarbonize the aviation industry.

In a preferred embodiment, the volumetric heat generation rate is greater than 0.1 MW/m$^3$ of fluidized bed, the volumetric heat coming from the electrically conductive particles, more preferably greater than 1 MW/m$^3$, in particular, greater than 3 MW/m$^3$.

In a preferred embodiment, the at least one fluidized bed reactor is devoid of heating means. For example, the at least one fluidized bed reactor comprises a vessel and is devoid of heating means located around or inside the vessel. For example, at least one fluidized bed reactor is devoid of heating means selected from ovens, gas burners, hot plates, or any combination thereof. For example, all the fluidized bed reactors are devoid of heating means selected from ovens, gas burners, hot plates, or any combination thereof.

For example, the content of electrically conductive particles is ranging from 15 wt. % to 95 wt. %, more preferably from 20 wt. % to 90 wt. %, even more preferably from 25 wt. % to 80 wt. % and most preferably from 30 wt. % to 75 wt. %.

For example, the content of electrically conductive particles based on the total weight of the bed is at least 12 wt. % based on the total weight of the particles of the bed; preferably, at least 15 wt. %, more preferably, at least 20 wt. %; even more preferably at least 25 wt. %, and most preferably at least 30 wt. % or at least 40 wt. % or at least 50 wt. % or at least 60 wt. %.

For example, the electrically conductive particles have a resistivity ranging from 0.005 to 400 Ohm·cm at 400° C., preferably ranging from 0.01 to 300 Ohm·cm at 400° C.; more preferably ranging from 0.05 to 150 Ohm·cm at 400° C. and most preferably ranging from 0.1 to 100 Ohm·cm at 400° C.

For example, the electrically conductive particles have a resistivity of at least 0.005 Ohm·cm at 400° C.; preferably of at least 0.01 Ohm·cm at 400° C., more preferably of at least 0.05 Ohm·cm at 400° C.; even more preferably of at least 0.1 Ohm·cm at 400° C., and most preferably of at least 0.5 Ohm·cm at 400° C.

For example, the electrically conductive particles have a resistivity of at most 400 Ohm·cm at 400° C.; preferably of at most 300 Ohm·cm at 400° C., more preferably of at most 200 Ohm·cm at 400° C.; even more preferably of at most 150 Ohm·cm at 400° C., and most preferably of at most 100 Ohm·cm at 400° C. The selection of the content of electrically conductive particles based on the total weight of the particles of the bed and of the electrically conductive particles of a given resistivity influence the temperature reached by the fluidized bed. Thus, in case the targeted temperature is not attained, the person skilled in the art may increase the density of the bed of particles, the content of electrically conductive particles based on the total weight of the particles of the bed and/or select electrically conductive particles with a lower resistivity to increase the temperature reach by the fluidized bed.

For example, the content of the particles of the catalytic composition is ranging from 15 wt. % to 95 wt. %, more preferably from 20 wt. % to 90 wt. %, even more preferably from 25 wt. % to 80 wt. % and most preferably from 30 wt. % to 75 wt. %.

For example, the density of the bed of particles is expressed as the void fraction. Void fraction or bed porosity is the volume of voids between the particles divided by the total volume of the bed. At the incipient fluidisation velocity, the void fraction is typically between 0.4 and 0.5. The void fraction can increase up to 0.98 in fast fluidised beds with lower values at the bottom of about 0.5 and higher than 0.9 at the top of the bed. The void fraction can be controlled by the linear velocity of the fluidising gas and can be decreased by recycling solid particles that are recovered at the top and send back to the bottom of the fluidized bed, which compensates for the entrainment of solid particles out of the bed.

The void fraction VF is defined as the volume fraction of voids in a bed of particles and is determined according to the following equation:

$$VF = \frac{Vt - Vp}{Vt} \tag{1}$$

wherein Vt is the total volume of the bed and is determined by $$Vt = AH \tag{2}$$

wherein A is the cross-sectional area of the fluidized bed and H is the height of the fluidized bed; and wherein Vp is the total volume of particles within the fluidized bed.

For example, the void fraction of the bed is ranging from 0.5 to 0.8; preferably ranging from 0.5 to 0.7, more preferably from 0.5 to 0.6. To increase the density of the bed of particles, the void fraction is to be reduced.

For example, the particles of the bed have an average particle size ranging from 5 to 300 μm as determined by sieving according to ASTM D4513-11, preferably ranging from 10 to 200 μm and more preferably ranging from 20 to 200 μm or from 30 to 150 μm.

Determination by sieving according to ASTM D4513-11 is preferred. In case the particles have an average size of below 20 μm the determination of the average size can also be done by Laser Light Scattering according to ASTM D4464-15.

For example, the electrically conductive particles of the bed have an average particle size ranging from 5 to 300 μm as determined by sieving according to ASTM D4513-11, preferably ranging from 10 to 200 μm and more preferably ranging from 30 to 150 μm.

In an embodiment, from 50 wt. % to 100 wt. % of the electrically conductive particles of the bed based on the total weight of the electrically conductive particles of the bed are one or more selected from metallic alloys, one or more non-metallic resistors, one or more metallic carbides, one or more metallic nitrides, one or more metallic phosphides, one or more carbon-containing particles, one or more superionic conductors, one or more phosphate electrolytes; preferably, from 60 wt. % to 100 wt. %; more preferably from 70 wt. % to 100 wt. %; even more preferably from 80 wt. % to 100 wt. % and most preferably from 90 wt. % to 100 wt. %.

With preference, the electrically conductive particles of the bed are or comprise one or more selected from metallic alloys, one or more non-metallic resistors, one or more metallic carbides, one or more metallic nitrides, one or more metallic phosphides, one or more carbon-containing particles, one or more superionic conductors; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

With preference, the electrically conductive particles of the bed are or comprise one or more selected from non-metallic resistors, one or more metallic carbides, one or more metallic nitrides, one or more metallic phosphides, one or more carbon-containing particles, one or more superionic conductors, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

As an alternative, the electrically conductive particles of the bed are one or more particles selected from one or more metallic alloys, one or more non-metallic resistors provided that the non-metallic resistor is not silicon carbide, one or more metallic carbides, one or more metallic nitrides, one or more metallic phosphides, one or more carbon-containing particles, one or more superionic conductors, one or more phosphate electrolytes, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more selected from one or more metallic alloys, one or more non-metallic resistors, one or more carbon-containing particles, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more selected from one or more non-metallic resistors, one or more carbon-containing particles, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, said one or more metallic alloys are selected from Ni—Cr, Fe—Ni—Cr, Fe—Ni—Al or a mixture thereof. With preference, when said metallic alloy comprises at least chromium, the chromium content is at least 15 mol. % of the total molar content of said metallic alloy comprising at least chromium, more preferably at least 20 mol. %, even more preferably at least 25 mol. %, most preferably at least 30 mol. %. Advantageously yet, the iron content in the metallic alloys is at most 2.0% based on the total molar content of the said metallic alloy, preferably at most 1.5 mol. %, more preferably at most 1.0 mol. %, even more preferably at most 0.5 mol. %.

For example, a non-metallic resistor is silicon carbide (SiC), molybdenum disilicide ($MoSi_2$), nickel silicide (NiSi), sodium silicide ($Na_2Si$), magnesium silicide ($Mg_2Si$), platinum silicide (PtSi), titanium silicide ($TiSi_2$), tungsten silicide ($WSi_2$) or a mixture thereof, preferably silicon carbide.

For example, said one or more metallic carbides are selected from iron carbide ($Fe_3C$) and/or molybdenum carbide (such as a mixture of MoC and $Mo_2C$).

For example, said one or more metallic nitrides are selected from zirconium nitride (ZrN), tungsten nitride (such as a mixture of $W_2N$, WN, and $WN_2$), vanadium nitride (VN), tantalum nitride (TaN), and/or niobium nitride (NbN).

For example, said one or more metallic phosphides are selected from copper phosphide ($Cu_3P$), indium phosphide (InP), gallium phosphide (GaP), sodium phosphide $Na_3P$), aluminium phosphide (AlP), zinc phosphide ($Zn_3P_2$) and/or calcium phosphide ($Ca_3P_2$).

For example, said one or more carbon-containing particles are selected from graphite, carbon black, petroleum coke, coke or any combination thereof.

For example, said one or more superionic conductors are selected from $LiAlSiO_4$, $Li_{10}GeP_2S_{12}$, $Li_{3.6}Si_{0.6}P_{0.4}O_4$, sodium superionic conductors (NaSICON), such as $Na_3Zr_2PSi_2O_{12}$, or sodium beta alumina, such as $NaAl_{11}O_{17}$, $Na_{1.6}Al_{11}O_{17.3}$, and/or $Na_{1.76}Li_{0.38}Al_{10.62}O_{17}$.

For example, said one or more phosphate electrolytes are selected from $LiPO_4$ or $LaPO_4$.

For example, the electrically conductive particles of the bed are or comprise a non-metallic resistor being silicon carbide.

For example, the electrically conductive particles of the bed are or comprise a mixture of a non-metallic resistor being silicon carbide and electrically conductive particles different from silicon carbide. The presence of electrically conductive particles different from silicon carbide in the bed is optional. It can be present as a starting material for heating the bed since it was found that the resistivity of silicon carbide at room temperature is too high to start heating the bed. Alternatively to the presence of electrically conductive particles different from silicon carbide, it is possible to provide heat to the reactor for a defined time to start the reaction.

For example, the silicon carbide is selected from sintered silicon carbide, nitride-bounded silicon carbide, recrystallised silicon carbide, reaction bonded silicon carbide and any mixture thereof. The type of silicon carbide material is selected according to the required heating power necessary for supplying the reaction heat of the catalytic dehydration of alcohols into one or more olefins.

For example, the electrically conductive particles of the bed are or comprise a mixture of a non-metallic resistor being silicon carbide and electrically conductive particles different from silicon carbide and the electrically conductive particles of the bed comprises from 10 wt. % to 99 wt. % of silicon carbide based on the total weight of the electrically conductive of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the electrically conductive particles of the bed are or comprise one or more metallic alloys; with preference, one or more metallic alloys are selected from Ni—Cr, Fe—Ni—Cr, Fe—Ni—Al or a mixture thereof.

With preference, when said metallic alloy comprises at least chromium, the chromium content is at least 15 mol. % of the total molar content of said metallic alloy comprising at least chromium, more preferably at least 20 mol. %, even more preferably at least 25 mol. %, most preferably at least 30 mol. %. Advantageously yet, the iron content in the metallic alloys is at most 2.0% based on the total molar content of said metallic alloy, preferably at most 1.5 mol. %, more preferably at most 1.0 mol. %, even more preferably at most 0.5 mol. %.

For example, the electrically conductive particles of the bed are or comprise a mixture of a non-metallic resistor being silicon carbide and particles different from silicon carbide wherein the particles different from silicon carbide are or comprise molybdenum disilicide; with preference, said molybdenum disilicide is molybdenum disilicide particles having an average particle size ranging from 5 to 300 µm as determined by sieving according to ASTM D4513-11, more preferably ranging from 10 to 200 µm and most preferably ranging from 30 to 150 µm.

For example, the catalytic dehydration of one or more alcohols having at least two carbon atoms into one or more olefins is conducted at a temperature ranging from 200° C. to 500° C., preferably from 240° C. to 490° C., more preferably from 260° C. to 480° C.

For example, the catalytic dehydration of one or more alcohols having at least two carbon atoms into olefins is performed at a pressure ranging between 0.05 MPa and 3 MPa, preferably between 0.05 MPa and 1.5 MPa, more preferably between 0.12 MPa and 0.8 MPa, or between 0.12 MPa and 0.5 MPa. This pressure is considered as a moderate pressure.

For example, the partial pressure of the alcohol-containing feedstock is ranging between 0.12 MPa and 0.7 MPa.

In an embodiment, said process comprises a step of pre-heating with a gaseous stream said fluidized bed reactor before conducting the catalytic dehydration of one or more alcohols having at least two carbon atoms into one or more olefins in the fluidized bed reactor; with preference, said gaseous stream is a stream of one or more inert gases and/or has a temperature comprised between 100° C. and 300° C. The said embodiment is of interest to bring energy to the system and/or when the particles of the bed have too high resistivity at room temperature to start the electro-heating of the bed. For example, the one or more inert gases are gases that do not provide any adverse effect on the catalyst. For example, the one or more inert gases are selected among nitrogen, argon, helium, saturated hydrocarbons having up to carbon atoms, or any combinations thereof. More preferably, the one or more inert gases are or comprise saturated hydrocarbons having up to 10 carbon atoms, even more preferably saturated hydrocarbons having from 3 to 7 carbons atoms, or from 4 to 6 carbon atoms. For example, the one or more inert gases are or comprise butane, pentane, naphtha, or any combinations thereof.

In an embodiment, said process comprises a step of diluting the alcohol-containing feedstock with one or more diluents. For example, said one or more diluents are selected from steam, hydrogen, methane, carbon dioxide, or any combinations thereof. The one or more diluents allows to manage the selectivity of the reaction.

The alcohol-containing feedstock comprises one or more alcohols having at least two carbon atoms and optionally one or more inert gas and/or one or more diluents. By specifying that the alcohol-containing feedstock comprises one or more alcohols having at least two carbons, it means that methanol, if nevertheless present into the alcohol-containing feedstock, cannot be converted into an olefin. With preference, the alcohol-containing feedstock does not comprise methanol. For example, the amount of the one or more alcohols having at least two carbon atoms in the alcohol-containing feedstock is ranging from 5 wt. % to 100 wt. % based on the total weight of the alcohol-containing feedstock. For example, the one or more alcohols of the alcohol-containing feedstock are or comprise one or more alcohols having from 2 to 10 carbon atoms. For example, the one or more alcohols of the alcohol-containing feedstock are or comprise ethanol, n-propanol, iso-propanol, n-butanol, sec-butanol, iso-butanol, tert-butanol, hexan-1-ol, hexan-2-ol, hexan-3-ol, 2-methylpentan-1-ol, 3-methylpentan-1-ol, 4-methylpentan-1-ol, 2-methylpentan-2-ol, 3-methylpentan-2-ol, 4-methylpentan-2-ol, 2-methylpentan-3-ol, 3-methylpentan-3-ol, 2,2-dimethylbutan-1-ol, 2-3-dimethylbutan-1-ol, 3,3-dimethylbutan-1-ol, 2,3-dimethylbutan-2-ol, 3,3-dimethylbutan-2-ol, 2-ethylbutan-1-ol or any combinations thereof. For example, the amount of the one or more inert gases in the alcohol-containing feedstock is ranging from 0 wt. % to 95 wt. % based on the total weight of the alcohol-containing feedstock. For example, the amount of the one or more diluents in the alcohol-containing feedstock is ranging from 0 wt. % to 95 wt. % based on the total weight of the alcohol-containing feedstock.

For example, the catalytic dehydration of one or more alcohols having at least two carbon atoms into one or more olefins is performed at a weight hourly space velocity of said reaction stream comprised between $0.1\ h^{-1}$ and $100\ h^{-1}$, preferably comprised between $1.0\ h^{-1}$ and $50\ h^{-1}$, more preferably comprised between $1.5\ h^{-1}$ and $10\ h^{-1}$, even more preferably comprised between $2.0\ h^{-1}$ and $6.0\ h^{-1}$. The weight hourly space velocity is defined as the ratio of mass flow of the reaction stream to the mass of solid particulate material in the fluidized bed.

In particular, the one or more products obtained in the present process may include one or more of olefins, water, unconverted alcohols if any, one or more inert gases if any and one or more diluents if any. For example, the one or more olefins are recovered by fractionation means and/or the one or more inert gases if any are recycled at the reactor inlet. For example, the unconverted alcohols if any are recycled at the reactor inlet.

In a preferred embodiment, the residence time of the alcohol-containing feedstock in the fluidised bed section of the reactor where the temperature is between 26° and 500° C., may range from 0.1 to 10 seconds.

For example, wherein the at least one fluidized bed reactor provided in step a) comprises a heating zone and a reaction zone and wherein the fluid stream provided in step b) is provided to the heating zone and optionally comprises one or more inert gases and/or one or more diluent gases, the step c) of heating the fluidized bed to a temperature ranging from 200° C. to 500° C. to conduct the endothermic catalytic dehydration of an alcohol-containing feedstock into one or more olefins, wherein the alcohol-containing feedstock comprises one or more alcohols having at least two carbon atoms, comprises the following sub-steps:

heating the fluidized bed to a temperature ranging from 200° C. to 500° C. by passing an electric current through the heating zone of the at least one fluidized bed, transporting the heated particles from the heating zone to the reaction zone, in the reaction zone, putting the heated particles in a fluidized state by passing upwardly through the said bed of the reaction zone a fluid stream comprising an alcohol-containing feedstock, and optionally one or more inert gases and/or one or more diluent gases, to obtain a fluidized bed and to conduct the endothermic catalytic dehydration of an alcohol-containing feedstock into one or more olefins, optionally, recovering the particles from the reaction zone and recycling them to the heating zone.

For example, the step of heating the fluidized bed is performed by passing an electric current at a voltage of at most 300 V through the fluidized bed, preferably at most 200 V, more preferably at most 150 V, even more preferably at most 120 V, most preferably at most 100 V, even most preferably at most 90 V.

The fluid stream may be a gaseous stream and/or a vaporized stream.

Step c) provides that the catalytic dehydration of an alcohol-containing feedstock into one or more olefins is performed on an alcohol-containing feedstock which implies that an alcohol-containing feedstock is provided.

For example, wherein the heating zone and the reaction zone are mixed (i.e., the same zone); the fluid stream provided in step b) comprises an alcohol-containing feedstock.

For example, wherein the heating zone and the reaction zone are separated zones, the fluid stream provided in step b) to the heating zone is devoid of an alcohol-containing feedstock. For example, wherein the process comprises providing at least one fluidized bed reactor being a heating zone and at least one fluidized bed reactor being a reaction zone, the fluid stream provided in step b) to the heating zone is devoid of an alcohol-containing feedstock and the fluid stream provided in step b) to the reaction zone comprises an alcohol-containing feedstock.

It is understood that the alcohol-containing feedstock is provided to the reaction zone and that when the heating zone is separated from the reaction zone, no alcohol-containing feedstock is provided to the heating zone. It is understood that in addition to the alcohol-containing feedstock provided to the reaction zone, steam can be provided to the reaction zone to reach the recommended steam to hydrocarbon ratio in the reaction zone as described above.

For example, the at least one fluidized bed reactor provided in step a) comprises a heating zone and a reaction zone, and wherein the step c) of heating the fluidized bed comprises the following sub-steps:
- pre-heating the fluidized bed to a temperature ranging from 100° C. to 300° C. by passing upwardly through the particles of the bed a fluidizing stream being a gaseous stream having a temperature ranging from 100° C. to 300° C.;
- heating the fluidized bed to a temperature ranging from 200° C. to 500° C. by passing an electric current through the heating zone of the at least one fluidized bed reactor,
- transporting the heated particles from the heating zone to the reaction zone,
- in the reaction zone, putting the heated particles in a fluidized state by passing upwardly through the said bed of the reaction zone a fluid stream comprising an alcohol-containing feedstock to obtain a fluidized bed and to conduct the endothermic catalytic dehydration of one or more alcohols having at least two carbon atoms into one or more olefins,
- optionally, recovering the particles from the reaction zone and recycling them to the heating zone.

To perform the catalytic reaction, the bed particles further comprise a catalyst, which is one or more solid acid catalysts. For example, the content of the particles of the catalytic composition is ranging from 15 wt. % to 90 wt. % of the particles of the bed, more preferably from 20 wt. % to 85 wt. %, even more preferably from 25 wt. % to 80 wt. % and most preferably from 30 wt. % to 75 wt. %.

For example, the one or more solid acid catalysts have a surface area ranging between 50 m$^2$/g and 800 m$^2$/g as determined by N$_2$ sorption measurements, preferably between 100 m$^2$/g and 750 m$^2$/g, more preferably between 150 m$^2$/g and 700 m$^2$/g.

For example, the one or more solid acid catalysts are one or more oxides. With preference, said one or more oxides are one or more oxides selected from γ-Al$_2$O$_3$, β-Al$_2$O$_3$, η-Al$_2$O$_3$, δ-Al$_2$O$_3$, amorphous Al$_2$O$_3$, chlorine-containing alumina, fluorine-containing alumina, phosphorus-containing alumina, ZrO$_2$, acid-treated zirconia, acid-treated titania, niobium oxide, tungsten oxide or any combinations thereof.

For example, the one or more solid acid catalysts are one or more mixed oxides. With preference, the one or more mixed oxides are selected from SiO$_2$—Al$_2$O$_3$, SiO$_2$—TiO$_2$, SiO$_2$—SnO$_2$, SiO$_2$—ZrO$_2$, SiO$_2$—BeO, SiO$_2$—MgO, SiO$_2$—CaO, SiO$_2$—SrO, SiO$_2$—ZnO, SiO$_2$—Ga$_2$O$_3$, SiO$_2$—Y$_2$O$_3$, SiO$_2$—La$_2$O$_3$, SiO$_2$—WO$_3$, SiO$_2$—ThO$_2$, Al$_2$O$_3$—MgO, Al$_2$O$_3$—ZnO, Al$_2$O$_3$—ThO$_2$, Al$_2$O$_3$—TiO$_2$, Al$_2$O$_3$—ZrO$_2$, Al$_2$O$_3$—MoO$_3$, Al$_2$O$_3$—WO$_3$, Al$_2$O$_3$—Cr$_2$O$_3$, Al$_2$O$_3$—Mn$_2$O$_3$, Al$_2$O$_3$—Fe$_2$O$_3$, TiO$_2$—MgO, TiO$_2$—ZnO, TiO$_2$—ZrO$_2$, TiO$_2$—SnO$_2$, TiO$_2$—Sb$_2$O$_5$, TiO$_2$—V$_2$O$_5$, TiO$_2$—Cr$_2$O$_3$, TiO$_2$—MoO$_3$, TiO$_2$—WO$_3$, WO$_3$-son$_2$, WO$_3$—ZrO$_2$, Nb$_2$O$_5$—Al$_2$O$_3$, Nb$_2$O$_5$—WO$_3$, Nb$_2$O$_5$—MoO$_3$, Nb$_2$O$_5$—ZrO$_2$, Nb$_2$O$_5$—TiO$_2$, TiO$_2$—Fe$_2$O$_3$ and any combinations thereof.

For example, the one or more solid acid catalysts are one or more phosphates. With preference, said one or more phosphates are one or more phosphates selected from titanium phosphate, zirconium phosphate, iron phosphate or any combinations thereof.

For example, the one or more solid acid catalysts are one or more zeolites selected from the group of MFI, MEL, MOR, FER, MTT, MWW, TON, EUO, HEU, MFS, and MRE families, and any combinations thereof.

For example, the one or more solid acid catalysts are one or more zeolites having a Si/Al ratio of at least 10 as determined by X-Ray fluorescence spectroscopy For example, the one or more solid acid catalysts are one or more silicoaluminophosphate molecular sieves selected from the group of AEI, CHA and AEL families, and any combinations thereof.

As regards the measurement of the catalyst acid sites it can either be defined as the ability to give protons as defined by Brönsted, or as the ability to accept an electron pair as defined by Lewis. The measurement of the acidity is performed via temperature-programmed desorption of ammonia or by infrared spectroscopy. Such methods are described in "Studies in Surface Science and Catalysis", Kozo TANABE, Makoto MISONO, Yoshio ON0, Hideshi HATTORI, Vol. 51, NEW SOLID ACIDS AND BASES-THEIR CATALYTIC PROPERTIES, by KODANSHA LTD. and ELSEVIER SCIENCE PUBLISHERS, 1989 and "Solid Acid Catalysis—From Fundamentals to Applications", Hideshi Hattori & Yoshio Ono, by Taylor & Francis Group, 2015.

For example, the one or more zeolites are steamed and then optionally leached before being used in step (c), so as to result of having one or more zeolites being dealuminated. In other words, the one or more zeolites comprise at least 10 wt. % of aluminum in less based on the one or more zeolites not being dealuminated.

For example, the one or more zeolites comprise a structure with at least one 10-membered ring.

For example, the one or more zeolites are selected from the group of MFI, MEL, MOR, FER, MTT, MWW, TON, EUO, HEU, MFS, and MRE families, and any combination thereof; with preference, the one or more zeolites are selected from the group of MFI, MEL families and any combinations thereof.

For example, the one or more zeolites further comprises boron.

For example, the one or more zeolites are one or more phosphorus-modified zeolites.

Advantageously, the one or more zeolites are in H-form. In other words, less than 50 wt. %, preferably less than 45 wt. % or less than 40 wt. %, based on the total weight of the one or more zeolites comprises one or more metallic ions preferably selected from Na, Mg, Ca, La, Ni, Ce, Zn, Co or any combination thereof.

According to a second aspect, the disclosure provides an installation to perform an endothermic catalytic dehydration of one or more alcohols having at least two carbon atoms into one or more olefins, according to the first aspect, said installation comprises i) an electrified fluidized bed unit with at least one fluidized bed reactor comprising:
at least two electrodes;
a reactor vessel;
one or more fluid nozzles for the introduction of an alcohol-containing feedstock comprising one or more alcohols having at least two carbon atoms and optionally one or more inert gases and/or one or more diluent gases within at least one fluidized bed reactor; and
a bed comprising particles;
ii) a product-recovery unit;
(iii) an olefin-transformation unit, wherein said olefin-transformation unit is selected from an olefin oligomerization unit, or an aromatic alkylation unit, or an olefin oligomerization and aromatic alkylation unit, wherein the product-recovery is downstream the electrified fluidized bed unit and upstream the olefin-transformation unit;
(iv) an optional hydrogenation unit, wherein said hydrogenation unit, when present, is downstream said olefin-transformation unit;
the installation is remarkable in that the particles of the bed comprise electrically conductive particles and particles of a catalytic composition, wherein at least 10 wt. % of the particles of the bed based on the total weight of the particle of the bed are electrically conductive, have a resistivity ranging from 0.001 Ohm·cm to 500 Ohm·cm at a temperature of 400° C., and wherein the catalytic composition comprises one or more solid acid catalysts.

With preference, the at least two electrodes comprise or are made of tantalum.

For example, the electrically conductive particles are or comprise one or more selected from one or more metallic alloys, one or more non-metallic resistors, one or more metallic carbides, one or more metallic nitrides, one or more metallic phosphides, one or more carbon-containing particles, one or more superionic conductors, one or more phosphate electrolytes, and any mixture thereof.

Advantageously, at least one fluidized bed reactor is devoid of heating means. For example, at least one fluidized bed reactor is devoid of heating means located around or inside the reactor vessel. For example, all the fluidized bed reactors are devoid of heating means. When stating that at least one of the fluidized bed reactors is devoid of "heating means", it refers to "classical' heating means, such as ovens, gas burners, hot plates and the like. There are no other heating means than the at least two electrodes of the fluidized bed reactor itself. For example, at least one fluidized bed reactor is devoid of heating means selected from ovens, gas burners, hot plates, or any combination thereof. For example, all the fluidized bed reactors are devoid of heating means selected from ovens, gas burners, hot plates, or any combination thereof.

In a preferred embodiment, the at least one fluidized bed reactor comprising at least two electrodes and a bed comprising particles is devoid of packing.

For example, the fluidizing gas is one or more diluent gases.

For example, the at least one reactor vessel has an inner diameter of at least 100 cm, preferably at least 200 cm, more preferably at least 300 cm.

With preference, the reactor vessel comprises a reactor wall made of materials that are corrosion-resistant materials and advantageously said reactor wall materials comprise nickel (Ni), SiAlON ceramics, yttria-stabilized zirconia (YSZ), tetragonal polycrystalline zirconia (TZP) and/or tetragonal zirconia polycrystal (TPZ).

With preference, one of the electrodes is the reactor vessel or the gas distributor and/or said at least two electrodes are made in stainless steel material or nickel-chromium alloys or nickel-chromium-iron alloys.

For example, the at least one fluidized bed reactor comprises a heating zone and a reaction zone, one or more fluid nozzles to provide an alcohol-containing feedstock to the reaction zone, and optional means to transport the particles of the bed from the reaction zone back to the heating zone.

For example, the installation comprises at least two fluidized bed reactors connected one to each other wherein at least one reactor of said at least two fluidized bed reactors is the heating zone and at least another reactor of said at least two fluidized bed reactors is the reaction zone. With preference, the installation comprises one or more fluid nozzles arranged to inject an alcohol-containing feedstock to the at least one fluidized bed reactor being the reaction zone, means to transport the particles of the bed from the heating zone to the reaction zone when necessary and optional means to transport the particles from the reaction zone back to the heating zone. This configuration is remarkable in that a given particle bed is common to at least two fluidized bed reactors.

For example, the at least one fluidized bed reactor is a single fluidized bed reactor wherein the heating zone is the bottom part of the fluidized bed reactor while the reaction zone is the top part of the fluidised bed reactor. With preference, the installation comprises one or more fluid nozzles to inject an alcohol-containing feedstock between the two zones. The diameter of the heating zone and reaction zone can be different to accomplish optimum conditions for heating in the bottom zone and optimum conditions for dehydration reaction in the top zone. Particles can move from the heating zone to the reaction zone by entrainment and the other way around from the reaction zone back to the heating zone by gravity. Optionally, particles can be collected from the upper heating zone and transferred by a separate transfer line back to the bottom heating zone.

For example, the at least one fluidized bed comprises at least two lateral zones being an outer zone and an inner zone wherein the outer zone is surrounding the inner zone, with the outer zone being the heating zone and the inner zone being the reaction zone. In a less preferred configuration, the outer zone is the reaction zone and the inner zone is the heating zone. With preference, the installation comprises one or more fluid nozzles to inject an alcohol-containing feedstock in the reaction zone.

In an embodiment, from 50 wt. % to 100 wt. % of the electrically conductive particles of the bed based on the total weight of the electrically conductive particles of the bed are one or more selected from one or more metallic alloys, one or more non-metallic resistors, one or more metallic carbides, one or more metallic nitrides, one or more metallic phosphides, one or more carbon-containing particles, one or more superionic conductors, one or more phosphate electrolytes, and any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

According to a third aspect, the disclosure provides the use of a bed comprising particles in at least one fluidized bed reactor to perform a catalytic dehydration of one or more alcohols having at least two carbon atoms into one or more olefins according to the first aspect, the use is remarkable in that the particles of the bed comprise electrically conductive particles and particles of a catalytic composition, wherein at least 10 wt. % of the particles of the bed based on the total weight of the particles of the bed are electrically conductive, have a resistivity ranging from 0.001 Ohm·cm to 500 Ohm·cm at a temperature of 400° C., and wherein the catalytic composition comprises one or more solid acid catalysts.

For example, the electrically conductive particles are or comprise one or more selected from one or more metallic alloys, one or more non-metallic resistors, one or more metallic carbides, one or more metallic nitrides, one or more metallic phosphides, one or more carbon-containing particles, one or more superionic conductors, one or more phosphate electrolytes, and any mixture thereof.

For example, the use comprises heating the bed comprising particles to a temperature ranging from 200° C. to 500° C. in a first reactor, transporting the heated particle bed from the first reactor to a second reactor and providing an alcohol-containing feedstock to the second reactor; with preference, at least the second reactor is a fluidized bed reactor and/or at least the second reactor is devoid of heating means; more preferably, the first reactor and the second reactor are fluidized bed reactors and/or the first and the second reactor are devoid of heating means. For example, the second reactor is devoid of electrodes.

In an embodiment, from 50 wt. % to 100 wt. % of the electrically conductive particles of the bed based on the total weight of the electrically conductive particles of the bed are one or more selected from one or more metallic alloys, one or more non-metallic resistors, one or more metallic carbides, one or more metallic nitrides, one or more metallic phosphides, one or more carbon-containing particles, one or more superionic conductors, one or more phosphate electrolytes, and any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

According to a fourth aspect, the disclosure provides the use of an installation comprising at least one fluidized bed reactor to perform a catalytic dehydration of one or more alcohols having at least two carbon atoms into one or more olefins, remarkable in that the installation is according to the second aspect. With preference, the use of an installation at least one fluidized bed reactor to perform a catalytic dehydration of one or more alcohols having at least two carbon atoms into one or more olefins in a process according to the first aspect.

The particular features, structures, characteristics or embodiments may be combined in any suitable manner, as would be apparent to a person skilled in the art from this disclosure, in one or more embodiments.

DETAILED DESCRIPTION

Figure 1:
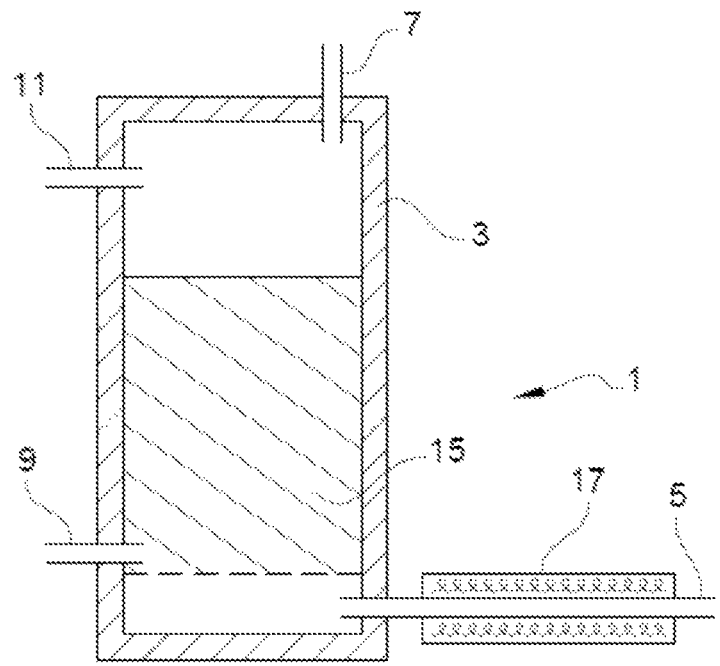
FIG. 1 illustrates an installation according to the prior art.

For the disclosure, the following definitions are given:
The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g., 1 to 5 can include 1, 2, 3, 4, 5 when referring to, for example, a number of elements, and can also include 1.5, 2, 2.75 and 3.80, when referring to, for example, measurements). The recitation of endpoints also includes the recited endpoint values themselves (e.g., from 1.0 to 5.0 includes both 1.0 and 5.0). Any numerical range recited herein is intended to include all sub-ranges subsumed therein.

Zeolite codes (e.g., CHA . . . ) are defined according to the "*Atlas of Zeolite Framework Types*", $6^{th}$ revised edition, 2007, Elsevier, to which the present application also refers.

The Si/Al atomic ratio of a zeolite corresponds to the amount of $SiO_2$ divided by the amount of $Al_2O_3$ taking into account the fact there are two atoms of aluminium for one atom of silicon. The silicon to aluminium ratio (also stated as SAR) corresponds to the amount of $SiO_2$ divided by the amount of $Al_2O_3$ notwithstanding the proportion of the Si atoms over the Al atoms in the chemical formula of the zeolite. Therefore, the value of the SAR always corresponds to twice the value of the Si/Al atomic ratio.

The present disclosure provides a process to perform a catalytic dehydration of one or more alcohols having at least two carbon atoms into one or more olefins, said process comprising the steps of:
  a) providing at least one fluidized bed reactor comprising at least two electrodes and a bed comprising particles;
  b) putting the particles of the bed in a fluidized state by passing upwardly through the said bed a fluid stream, to obtain a fluidized bed;
  c) heating the fluidized bed to a temperature ranging from 200° C. to 500° C. to conduct the catalytic dehydration of an alcohol-containing feedstock into one or more olefins, wherein the alcohol-containing feedstock comprises one or more alcohols having at least two carbon atoms; and
  d) optionally, recovering the one or more olefins;
the process is remarkable in that the particles of the bed comprise electrically conductive particles and particles of a catalytic composition, wherein at least 10 wt. % of the particles based on the total weight of the particles of the bed are electrically conductive and have a resistivity ranging from 0.001 Ohm·cm to 500 Ohm·cm at of 400° C.; wherein the catalytic composition comprises one or more solid acid catalysts; in that the step c) of heating the fluidized bed is performed by passing an electric current through the fluidized bed.

For example, the one or more olefins have the same number of carbons as the one or more alcohols. That is the reason why if methanol is present in the alcohol-containing feedstock, said methanol cannot be converted into olefins. With preference, the alcohol-containing feedstock does not comprise methanol.

For example, the electrically conductive particles of the bed are or comprise one or more selected from one or more carbon-containing particles, one or more metallic alloys, one or more non-metallic resistors, one or more metallic carbides, one or more metallic nitrides, one or more metallic phosphides, one or more carbon-containing particles, one or more superionic conductors, one or more phosphate electrolytes, and any mixture thereof.

In an embodiment, from 50 wt. % to 100 wt. % of the electrically conductive particles of the bed based on the total weight of the electrically conductive particles of the bed are one or more selected from one or more metallic alloys, one or more non-metallic resistors, one or more metallic carbides, one or more metallic nitrides, one or more metallic phosphides, one or more carbon-containing particles, one or more superionic conductors, one or more phosphate electrolytes, and any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

The fluid stream may be a gaseous stream and/or a vaporized stream.

For example, the step of heating the fluidized bed is performed by passing an electric current at a voltage of at most 300 V through the fluidized bed, preferably at most 200 V, more preferably at most 150 V, even more preferably at most 120 V, most preferably at most 100 V, even most preferably at most 90 V.

The solid particulate material in the fluidized bed reactor is typically supported by a porous plate, a perforated plate, a plate with nozzles or chimneys, known as a distributor. The fluid is then forced through the distributor up and travelling through the voids between the solid particulate material. At lower fluid velocities, the solids remain settled as the fluid passes through the voids in the material, known as a packed bed reactor. As the fluid velocity is increased, the particulate solids will reach a stage where the force of the fluid on the solids is enough to counterbalance the weight of the solid particulate material. This stage is known as incipient fluidization and occurs at this minimum fluidization velocity. Once this minimum velocity is surpassed, the contents of the reactor bed begin to expand and become fluidized. Depending on the operating conditions and properties of the solid phase various flow regimes can be observed in such reactors. The minimum fluidization velocity needed to achieve bed expansion depends upon the size, shape, porosity and density of the particles and the density and viscosity of the upflowing fluid.

P. R. Gunjal, V. V. Ranade, in Industrial Catalytic Processes for Fine and Specialty Chemicals, (2016) reads that four different categories of fluidization based on the mean particle have been differentiated by Geldart that determine the fluidization regimes:

type A, aeratable fluidization (medium size, medium-density particles which are easier to fluidize; Particles of typically 30-100 μm, density ~1500 kg/m$^3$);

type B, sand-like fluidization (heavier particles which are difficult to fluidize; Particles of typically 100-800 μm, density between 1500 and 4000 kg/m$^3$);

type C, cohesive fluidization (typical powder-like solid particle fluidization; Fine-size particles (~20 μm) with a dominance of intraparticle or cohesive forces); and type D, spoutable fluidization (large density and larger particle ~1-4 mm, dense and spoutable).

Fluidization may be broadly classified into two regimes (Fluid Bed Technology in Materials Processing, 1999 by CRC Press): homogeneous fluidization and heterogeneous fluidization. In homogeneous or particulate fluidization, particles are fluidized uniformly without any distinct voids. In heterogeneous or bubbling fluidization, gas bubbles devoid of solids are distinctly observable. These voids behave like bubbles in gas-liquid flows and exchange gas with the surrounding homogeneous medium with a change in size and shape while rising in the medium. In particulate fluidization, the bed expands smoothly with substantial particle movement and the bed surface is well defined. Particulate fluidization is observed only for Geldart-A type particles. A bubbling fluidization regime is observed at much higher velocities than homogeneous fluidization, in which distinguishable gas bubbles grow from the distributor, may coalesce with other bubbles and eventually burst at the surface of the bed. These bubbles intensify the mixing of solids and gases and bubble sizes tend to increase further with a rise in fluidization velocity. A slugging regime is observed when the bubble diameter increases up to the reactor diameter. In a turbulent regime, bubbles grow and start breaking up with the expansion of the bed. Under these conditions, the top surface of the bed is no longer distinguishable. In fast fluidization or pneumatic fluidization, particles are transported out of the bed and need to be recycled back into the reactor. No distinct bed surface is observed.

Fluidized bed reactors have the following advantages:

Uniform Particle Mixing: Due to the intrinsic fluid-like behaviour of the solid particulate material, fluidized beds do not experience poor mixing as in packed beds. The elimination of radial and axial concentration gradients also allows for better fluid-solid contact, which is essential for reaction efficiency and quality.

Uniform Temperature Gradients: Many chemical reactions require the addition or removal of heat. Local hot or cold spots within the reaction bed are avoided in a fluidized situation.

Ability to Operate the Reactor Continuously: The fluidized bed nature of these reactors allows for the ability to continuously withdraw products and introduce new reactants into the reaction vessel. On top of continuous operation of the chemical reactions, the fluidized bed allows also to continuously or at given frequency withdraw solid material or add continuously or at given frequency new fresh solid material thanks to the flowable solid particulate material.

Heat can be produced by passing an electrical current through a conducting material that has sufficiently high resistivity (the resistor) to transform electricity into heat. Electrical resistivity (also called specific electrical resistance or volume resistivity, is an intrinsic property independent of shape and size) and its inverse, electrical conductivity, is a fundamental property of a material that quantifies how strongly it resists or conducts electric current (SI unit of electrical resistivity is the ohm-meter ($\Omega \cdot$m) and for conductivity Siemens per meter (S/m)).

When electricity is passed through a fixed bed of electrically conducting particulate solids, having a sufficient resistivity, the bed offers resistance to the flow of current; this resistance depends on many parameters, including the nature of the solid, the nature of the linkages among the particles within the bed, the bed voidage, the bed height, the electrode geometry, etc. If the same fixed bed is fluidized by passing gas, the resistance of the bed increases; the resistance offered by the conducting particles generates heat within the bed and can maintain the bed in isothermal conditions (termed an electrothermal fluidized bed or electrofluid reactor). In many high-temperature reactions, electrofluid reactors offer in situ heating during the reaction and are particularly useful for operating endothermic reactions and hence save energy because no external heating or transfer of heat is required. It is a prerequisite that at least part of the solid particulate material is electrically conducting but non-conducting solid particulates can be mixed and still result in enough heat generation. Such non-conducting or very high resistivity solids can play a catalytic role in the chemical conversion. The characteristics of the bed material determine the resistance of an electrothermal fluidized bed furnace; as this is a charge resistor type of heat generation, the specific resistivity of the particles affects the bed resistance. The size, shape, composition, and size distribution of the particles also influence the magnitude of the bed resistance. Also, when the bed is fluidized, the voids generated between the particles increases the bed resistance. The total resistance of the bed is the sum of two components, e.g., the electrode contact-resistance (i.e., the resistance between the electrode and the bed) and the bed resistance. A large contact-resistance will cause extensive local heating in the vicinity of the electrode while the rest of the bed stays rather cool. The following factors determine the contact-resistance: current density, fluidization velocity, type of bed material, electrode size and the type of material used for the electrodes. The electrode compositions can be advantageously metallic like iron, cast iron or other steel alloys, copper or a copper-based alloy, nickel or a nickel-based alloy or refractory like metal, intermetallics or an alloy of Zr, Hf, V, Nb, Ta, Cr, Mo, W or ceramic-like carbides, or nitrides. The area of contact between the bed material and the electrodes can be adjusted, depending on the electrode submergence and the amount of particulate material in the fluidized bed. Hence, the electrical resistance and the power level can be manipulated by adjusting these variables. Advantageously, to prevent overheating of the electrodes compared to the fluidised bed, the resistivity of the electrode should be lower (and hence the joule heating) than of the particulate material of the fluidized bed. In a preferred embodiment, the electrodes can be cooled by passing a colder fluid inside or outside the electrodes. Such fluids can be any liquid that vaporises upon a heating, gas stream or can be a part of the colder feedstock that first cools the electrode before entering the fluidised bed.

Bed resistance can be predicted by the ohmic law. The mechanism of current transfer in fluidized beds is believed to occur through current flow along continuous chains of conducting particles at low operating voltages. At high voltages, a current transfer occurs through a combination of chains of conducting particles and arcing between the electrode and the bed as well as particle-to-particle arcing that might ionize the gas, thereby bringing down the bed resistance. Arcing inside the bed, in principle, is not desirable as it would lower the electrical and thermal efficiency. The gas velocity impacts strongly the bed resistance, a sharp increase in resistance from the settled bed onward when the gas flow rate is increased; a maximum occurred close to the incipient fluidization velocity, followed by a decrease at higher velocities. At gas flow rates sufficient to initiate slugging, the resistance again increased. Average particle size and shape impact resistance as they influence the contacts points between particles. In general, the bed resistivity increases 2 to 5 times from a settled bed (e.g., 20 Ohm·cm for graphite) to the incipient fluidisation (60 Ohm·cm for graphite) and 10 to 40 times from a settled bed to twice (300 Ohm·cm for graphite) the incipient fluidisation velocity. Non or less-conducting particles can be added to conducting particles. If the conducting solid fraction is small, the resistivity of the bed would increase due to the breaking of the linkages in the chain of conducting solids between the electrodes. If the non-conducting solid fraction is finer in size, it would fill up the interstitial gaps or voidage of the larger conducting solids and hence increase the resistance of the bed.

In general, for a desired high heating power, a high current at a low voltage is preferred. The power source can be either AC or DC. Voltages applied in an electrothermal fluidized bed are typically below 100 V to reach enough heating power. The electrothermal fluidized bed can be controlled in the following three ways:

1. Adjusting the gas flow: Because the conductivity of the bed depends on the extent of voidage or gas bubbles inside the bed, any variation in the gas flow rate would change the power level; hence the temperature can be controlled by adjusting the fluidizing gas flow rate. The flow rate required for optimum performance corresponds to a velocity which equals or slightly exceeds the minimum fluidization velocity.

2. Adjusting the electrode submergence: The power level can also be controlled by varying the electrode immersion level inside the bed because the conductivity of the bed is dependent on the area of contact between the conducting particles and the electrode: the surface area of the electrode available for current flow increases with electrode submergence, leading to a reduction in overall resistance.

3. Adjusting the applied voltage: although changing the power level by using the first two methods is often more affordable or economical than increasing the applied voltage, however in electrothermal fluidized beds three variables are available to control the produced heating power.

The wall of the reactor is generally made of ceramics (like SiC), high-melting metals or alloys as it is versatile and compatible with many high-temperature reactions of industrial interest. The atmosphere for the reaction is often restricted to the neutral or the reducing type as an oxidising atmosphere can combust carbon materials or create a non-conducting metal oxide layer on top of metals or alloys. The wall and/or the distribution plate itself can act as an electrode for the reactor. The fluidized solids can be molybdenum disilicide, silicon carbide or any other high-melting-point, electrically conducting particles. The other electrodes, which is usually immersed in the bed, can also be a high-melting-point metal, intermetallics or alloys.

It may be advantaged to generate the required reaction heat by heating the conductive particles and/or catalyst particles in a separate zone of the reactor where little or substantially no feedstock hydrocarbons are present, but only diluent gases. The benefit is that the appropriate conditions of fluidization to generate heat by passing an electrical current through a bed of conductive particles can be optimized whereas the optimal reaction conditions during hydrocarbon transformation can be selected for the other zone of the reactor. Such conditions of optimal void fraction and linear velocity might be different for heating purposes and chemical transformation purposes.

In an embodiment of the present disclosure, the installation comprises of two zones arranged in series namely a first zone being a heating zone and a second zone being a reaction zone, where the conductive particles and catalyst particles are continuously moved or transported from the first zone to the second zone and vice versa. The first and second zones can be different parts of a fluidized bed or can be located in separate fluidized beds reactors connected one to each other.

In the said embodiment, the process to perform a catalytic dehydration of one or more alcohols having at least two carbon atoms into one or more olefins, said process comprising the steps of:
a) providing at least one fluidized bed reactor comprising at least two electrodes and a bed comprising particles;
b) putting the particles in a fluidized state by passing upwardly through the said bed a fluid stream, to obtain a fluidized bed;
c) heating the fluidized bed to a temperature ranging from 200° C. to 500° C. to conduct the catalytic dehydration of an alcohol-containing feedstock into one or more olefins, wherein the alcohol-containing feedstock comprises one or more alcohols having at least two carbon atoms; and
d) optionally, recovering the one or more olefins;
wherein at least 10 wt. % of the particles based on the total weight of the particles of the bed are electrically conductive particles, have a resistivity ranging from 0.001 Ohm·cm to 500 Ohm·cm at 400° C.; wherein the at least one fluidized bed reactor provided in step a) comprises a heating zone and a reaction zone and wherein the fluid stream provided in step b) is provided to the heating zone and comprises optional one or more diluent gases and/or one or more inert gases and the step c) of heating the fluidized bed to a temperature ranging from 200° C. to 500° C. to conduct the catalytic dehydration of an alcohol-containing feedstock into one or more olefins comprises the following sub-steps:
heating the fluidized bed to a temperature ranging from 200° C. to 500° C. by passing an electric current through the heating zone of the at least one fluidized bed,
transporting the heated particles from the heating zone to the reaction zone,
in the reaction zone, putting the heated particles in a fluidized state by passing upwardly through the said bed of the reaction zone a fluid stream comprising an alcohol-containing feedstock and optional diluent gases to obtain a fluidized bed and to conduct the endothermic catalytic dehydration of an alcohol-containing feedstock into one or more olefins,
optionally, recovering the particles from the reaction zone and recycling them to the heating zone.

For example, the electrically conductive particles are or comprise one or more selected from one or more metallic alloys, one or more non-metallic resistors, one or more metallic carbides, one or more metallic nitrides, one or more metallic phosphides, one or more carbon containing particles, one or more superionic conductors, one or more phosphate electrolytes, and/or any mixture thereof.

For example, the one or more inert gases are selected among nitrogen, carbon dioxide, argon, helium, saturated hydrocarbons having up to 10 carbon atoms, or any combination thereof. More preferably, the one or more inert gases are or comprise saturated hydrocarbons having up to 10 carbon atoms, even more preferably saturated hydrocarbons having from 3 to 7 carbons atoms, or from 4 to 6 carbon atoms. For example, the one or more inert gases are or comprise butane, pentane, naphtha, or a combination thereof.

For example, said one or more diluents are selected from steam, hydrogen, methane or any combination thereof.

The fluid stream may be a gaseous stream and/or a vaporized stream.

For example, the at least one fluidized bed reactor is at least two fluidized bed reactors connected one to each other wherein at least one of said at least two fluidized bed reactors is the heating zone and at least another of said at least two fluidized bed reactors is the reaction zone. With preference, the at least one fluidized bed reactor being the heating zone comprises gravitational or pneumatic transport means to transport the particles from the heating zone to the reaction zone and/or the installation comprises means arranged to inject an alcohol-containing feedstock to the at least one fluidized bed reactor being the reaction zone. The installation is devoid of means to inject an alcohol-containing feedstock to the at least one fluidized bed reactor being the heating zone.

For example, the at least one fluidized bed reactor is a single fluidized bed reactor wherein the heating zone is the bottom part of the fluidized bed reactor while the reaction zone is the top part of the fluidised bed reactor. With preference, the installation comprises means to inject an alcohol-containing feedstock and/or diluent between the two zones. The diameter of the heating zone and reaction zone can be different in order to accomplish optimum conditions for heating in the bottom zone and optimum conditions for hydrocarbon conversion in the top zone. Particles can move from the heating zone to the reaction zone by entrainment and the other way around from the reaction zone back to the heating zone by gravity. Optionally, particles can be collected from the upper heating zone and transferred by a separate transfer line back to the bottom heating zone.

Step c) provides that the catalytic dehydration of one or more alcohols having at least two carbon atoms into one or more olefins is performed on an alcohol-containing feedstock which implies that an alcohol-containing feedstock is provided. It is understood that the alcohol-containing feedstock is provided to the reaction zone and that when the heating zone is separated from the reaction zone then, with preference, no alcohol-containing feedstock is provided to the heating zone. When the heating zone and the reaction zone are mixed (i.e., the same zone); the fluid stream provided in step b) comprises an alcohol-containing feedstock.

The Bed Comprising Particles—Catalyst Particles

To perform the catalytic reaction, the bed particles further comprise a catalyst which is one or more solid acid catalysts. For example, the content of said catalyst particles is ranging from 15 wt. % to 90 wt. % based on the total weight of the particles of the bed, more preferably from 20 wt. % to 85 wt. %, even more preferably from 25 wt. % to 80 wt. % and most preferably from 30 wt. % to 75 wt. %.

For example, the one or more solid acid catalysts have a surface area ranging between 50 m$^2$/g and 800 m$^2$/g as determined by $N_2$ sorption measurements, preferably between 100 m$^2$/g and 750 m$^2$/g, more preferably between 150 m$^2$/g and 700 m$^2$/g.

The catalyst employed in the bed may be any one of wide variety of dehydration catalysts. Such catalysts are generally known in the art, and no details in this respect are deemed necessary for a complete understanding of the present invention. As illustrative dehydration catalysts, there may be mentioned: alumina, silica-alumina, activated clays, zeolites, modified zeolites.

More specifically, the catalyst composition comprises one or more zeolites and/or one or more silicoaluminophosphate molecular sieves. With preference, the one or more zeolites have a Si/Al ratio of at least 10 as determined by XRF spectroscopy, more preferably of at least 15, even more preferably of at least 50, most preferably of at least 100, even most preferably of at least 150, or of at least 180, or of at least 200. With preference, the one or more zeolites have a Si/Al ratio of at most 1000 as determined by XRF spectroscopy. For example, the one or more zeolites have a Si/Al ratio ranging between 10 and 1000 as determined by XRF spectroscopy, or between 15 and 1000, or between 50 and 1000, or between 100 and 1000, or between 180 and 1000, or between 200 and 1000. In this specification, the term "Si/Al ratio", or "silicon/aluminium atomic ratio", or "silicon/aluminium ratio" is intended to mean the Si/Al atomic ratio of the overall material, which may be determined by elemental analysis upon dissolution of the material or by X-ray fluorescence (XRF) spectroscopy. In particular, for crystalline silicate materials, the stated Si/Al ratios apply not just to the Si/Al framework of the crystalline silicate but rather to the whole material.

With preference, the one or more zeolites have relatively low acidity. The acidity of the catalyst or of the one or more zeolites can be determined by temperature programmed desorption (TPD) of ammonia where the amount of residual ammonia on the catalyst following contact of the catalyst with ammonia which adsorbs to the acid sites on the catalyst with subsequent ammonium desorption at elevated temperature measured by differential thermogravimetric analysis.

For example, the one or more zeolites are steamed and then optionally leached before being used in step (c), so as to result of having one or more zeolites being dealuminated. In other words, the one or more zeolites comprise at least 10% of aluminum in less based on the one or more zeolites not being dealuminated. With preference, the one or more zeolites are steamed at a temperature ranging between 425° C. and 870° C., more preferably ranging between 540° C. and 815° C., and/or at atmospheric pressure (i.e., about 0.1 MPa) and/or at a water partial pressure ranging from 13 kPa to 200 kPa. Preferably, the steaming is conducted in an atmosphere comprising from 5 to 100 vol. % steam based on the total volume of the atmosphere. The steam preferably comprises from 5 to 100 vol. % of steam along with from 0 to 95 vol. % of an inert gas based on the total volume of the steam. For example, the inert gas is nitrogen. A more preferred atmosphere comprises 72 vol. % of steam and 28 vol. % nitrogen based on the total volume of the atmosphere, i.e. 72 kPa steam at a pressure of one atmosphere. The steaming is preferably carried out for a period ranging from 1 to 200 hours, more preferably from 20 hours to 100 hours. As stated above, the steam treatment tends to reduce the amount of tetrahedral aluminium in the crystalline silicate framework, by forming alumina.

For example, the one or more zeolites comprise a structure with at least one 10-membered ring.

For example, the one or more zeolites are selected from the group of MFI, MEL, MOR, FER, MTT, MWW, TON, EUO, HEU, MFS, and MRE families, and any combination thereof; with preference, the one or more zeolites are selected from the group of MFI, MEL, FER, MTT, MWW, TON, EUO, MFS, and MRE families and any combinations thereof; more preferably, the one or more zeolites are selected from the group of MFI, MEL, and any combinations thereof.

For example, when the zeolite is MFI, it is preferred that the MFI zeolite has a Si/Al ratio of at least 100 as determined by X-Ray fluorescence spectroscopy of the one or more zeolites under their solid form.

For example, when the zeolite is FER, it is preferred that the FER zeolite has a Si/Al ratio of at least 10 as determined by X-Ray fluorescence spectroscopy of the one or more zeolites under their solid form, more preferably of at least 15.

At a Si/Al ratio above the values mentioned here, there is essentially a dehydration of the alcohol to olefin and almost no side reactions which could lead to aldehydes, to saturated hydrocarbons or any undesirable component.

With preference, zeolites from the MFI family are one or more selected from ZSM-5, silicalite-1, boralite C, or TS-1; more preferably, the zeolite from the MFI family are one or more selected from ZSM-5 or silicalite-1; even more preferably, the zeolite from the MFI family is ZSM-5.

With preference, zeolites from the MEL family are one or more selected from ZSM-11, silicalite-2, boralite D, TS-2, or SSZ-46; more preferably, the zeolite from the MEL family is ZSM-11.

With preference, a zeolite from the MOR family is UZM-14.

With preference, zeolites from the FER family are one or more selected from ferrierite, FU-9, or ZSM-35.

With preference, a zeolite from the MTT family is ZSM-23.

With preference, zeolites from the MWW family are one or more selected from MCM-22, PSH-3, ITQ-1, or MCM-49.

With preference, zeolites from the TON family are one or more selected from ZSM-22, Theta-1, or NU-10.

With preference, zeolites from the EUO family are selected from ZSM-50, or EU-1.

With preference, zeolites from the HEU family is clinoptilolite.

With preference, a zeolite from the MFS family is ZSM-57.

With preference, a zeolite from the MRE family is ZSM-48.

For example, the one or more zeolites further comprises boron.

For example, the one or more zeolites are one or more phosphorus-modified zeolites.

For example, the one or more zeolites are dealuminated zeolites.

Advantageously, the one or more zeolites are in H-form. In other words, less than 50 wt. %, preferably less than 45 wt. % or less than 40 wt. %, based on the total weight of the one or more zeolites comprises one or more metallic ions preferably selected from Na, Mg, Ca, La, Ni, Ce, Zn, Co or any combination thereof.

The following description gives more detail about the one or more zeolites (i.e., about the one or more crystalline silicate).

The one or more zeolites are microporous crystalline inorganic polymers based on a framework of $XO_4$ tetrahedra linked to each other by sharing of oxygen ions, where X may be trivalent (e.g. Al, B, . . . ) or tetravalent (e.g. Ge, Si, . . . ). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bidirectional intersecting pore system with the following pore diameters: a straight channel along [010]:0.53-0.56 nm and a sinusoidal channel along [100]:0.51-0.55 nm. Crystalline silicates with the MEL structure possess a bidirectional intersecting straight pore system with straight channels along having pore diameters of 0.53-0.54 nm.

In a more specific embodiment, the crystalline silicate catalyst is dealuminated by heating the catalyst in steam to remove aluminium from the crystalline silicate framework and extracting aluminium from the catalyst by contacting the catalyst with a complexing agent for aluminium to remove from pores of the framework alumina deposited therein during the steaming step thereby to increase the silicon/aluminium atomic ratio of the catalyst. The catalyst having a high silicon/aluminium atomic ratio for use in the catalytic process of the present disclosure is manufactured by removing aluminium from a commercially available crystalline silicate. By way of example a typical commercially available silicalite has a silicon/aluminium atomic ratio of around 120. In accordance with the present disclosure, the commercially available crystalline silicate is modified by a steaming process which reduces the tetrahedral aluminium in the crystalline silicate framework and converts the aluminium atoms into octahedral aluminium in the form of amorphous alumina. Although in the steaming step aluminium atoms are chemically removed from the crystalline silicate framework structure to form alumina particles, those particles can cause partial obstruction of the pores or channels in the framework. This could inhibit the dehydration process of the present disclosure. Accordingly, following the steaming step, the crystalline silicate can be subjected to a leaching, namely to an extraction step wherein amorphous alumina is removed from the pores and the micropore volume is, at least partially, recovered. The physical removal, by a leaching step, of the amorphous alumina from the pores by the formation of a water-soluble aluminium complex yields the overall effect of de-alumination of the crystalline silicate. In this way by removing aluminium from the crystalline silicate framework and then removing alumina formed therefrom from the pores, the process aims at achieving a substantially homogeneous de-alumination throughout the whole pore surfaces of the catalyst. This reduces the acidity of the catalyst. The reduction of acidity ideally occurs substantially homogeneously throughout the pores defined in the crystalline silicate framework. Following the steaming, the extraction process is performed in order to de-aluminate the catalyst by leaching. The aluminium is preferably extracted from the crystalline silicate by a complexing agent which tends to form a soluble complex with alumina. The complexing agent is preferably in an aqueous solution thereof. The complexing agent may comprise an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g., the sodium salt) or a mixture of two or more of such acids or salts. The complexing agent may comprise an inorganic acid such as nitric acid, halogenic acids, sulphuric acid, phosphoric acid or salts of such acids or a mixture of such acids. The complexing agent may also comprise a mixture of such organic and inorganic acids or their corresponding salts. The complexing agent for aluminium preferably forms a water-soluble complex with aluminium, and in particular removes alumina which is formed during the steam treatment step from the crystalline silicate. A particularly preferred complexing agent may comprise an amine, preferably ethylene diamine tetraacetic acid (EDTA) or a salt thereof, in particular the sodium salt thereof. In a preferred embodiment, the framework silicon/aluminium ratio is increased by this process to a value of from about 150 to 1000, more preferably from at least 200 to 1000.

Following the aluminium leaching step, the crystalline silicate may be subsequently washed, for example with distilled water, and then dried, preferably at an elevated temperature, for example around 110° C.

Additionally, if during the preparation of the catalysts of the disclosure alkaline or alkaline earth metals have been used, the molecular sieve might be subjected to an ion-exchange step. Conventionally, ion-exchange is done in aqueous solutions using ammonium salts or inorganic acids.

Following the de-alumination step, the catalyst can be thereafter calcined, for example at a temperature of from 400 to 800° C. and/or at an atmospheric pressure and/or for a period ranging from 1 to 10 hours.

The crystalline silicate can be subjected to various treatments before use in the dehydration including, ion exchange, modification with metals (in a not restrictive manner alkali, alkali-earth, transition, or rare earth elements), external surface passivation, modification with phosphorus-compounds, steaming, acid treatment or other dealumination methods, or combination thereof.

For example, the one or more silicoaluminophosphate molecular sieves selected from the group of AEI, CHA and AEL families, and any combinations thereof.

With preference, one silicoaluminophosphate molecular sieve selected from AEI family is SAPO-18.

With preference, one silicoaluminophosphate molecular sieve selected from CHA family is SAPO-34.

With preference, one silicoaluminophosphate molecular sieve selected from AEL family is SAPO-11.

The SAPO molecular sieve is based on the ALPO, having essentially an Al/P ratio of 1 atom/atom. During the synthesis silicon precursor is added and insertion of silicon in the ALPO framework results in an acid site at the surface of the micropores of the 10-membered ring sieve. The silicon content ranges from 0.1 to 10 atom % (Al+P+Si is 100).

In another specific embodiment the one or more solid acid catalysts, and preferentially the one or more zeolites, are mixed with a binder, preferably an inorganic binder, and shaped to a desired shape, e.g. pellets. The binder is selected so as to be resistant to the temperature and other conditions employed in the dehydration process of the disclosure. The binder is an inorganic material selected from clays, silica, metal silicates, metal oxides such as $ZrO_2$ and/or metals, or gels including mixtures of silica and metal oxides. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present disclosure comprises silica. The relative proportions of the finely divided crystalline silicate material and the inorganic oxide matrix of the binder can vary widely. Typically, the binder content ranges from 5 to 95 wt. % based on the total weight of the composite catalyst (the composite catalyst being the mixture between the one or more solid acid materials and the binder), more typically from 20 to 50 wt. % by weight, based on the weight of the composite catalyst. Such a mixture of crystalline silicate and an inorganic oxide binder is also referred to as a formulated crystalline silicate. In mixing the catalyst with a binder, the catalyst may be formulated into spheres or a spray-dried powder.

Spherical shapes can be made in rotating granulators or by oil-drop technique. Small spheres can further be made by spray-drying a catalyst-binder suspension. Thereafter, the formulated crystalline silicate is calcined in air or an inert gas, typically at a temperature of from 200 to 900° C. for a period of from 1 to 48 hours.

The binder preferably does not contain any aluminium compounds, such as alumina. This is because as mentioned above the preferred catalyst for use in the invention is de-aluminated to increase the silicon/aluminium ratio of the crystalline silicate. The presence of alumina in the binder yields other excess alumina if the binding step is performed prior to the aluminium extraction step. If the aluminium-containing binder is mixed with the crystalline silicate catalyst following aluminium extraction, this re-aluminates the catalyst.

In addition, the mixing of the catalyst with the binder may be carried out either before or after the steaming and extraction steps.

In another embodiment the catalyst is a crystalline silicate catalyst having a monoclinic structure, which has been for example produced by a process comprising providing a crystalline silicate of the MFI-type having a silicon/aluminium atomic ratio lower than 80; treating the crystalline silicate with steam and thereafter leaching aluminium from the zeolite by contact with an aqueous solution of a leachant to provide a silicon/aluminium atomic ratio in the catalyst of at least 180 whereby the catalyst has a monoclinic structure. Preferably, in the steam treatment step the temperature is from 425 to 870° C., more preferably from 540 to 815° C., and/or at a water partial pressure of from 13 to 200 kPa. Preferably, the aluminium is removed by leaching to form an aqueous soluble compound by contacting the zeolite with an aqueous solution of a complexing agent for aluminium which tends to form a soluble complex with alumina.

In accordance with this preferred process for producing monoclinic crystalline silicate, the starting crystalline silicate catalyst of the MFI-type has an orthorhombic symmetry and a relatively low silicon/aluminium atomic ratio which can have been synthesized without any organic template molecule and the final crystalline silicate catalyst has a relatively high silicon/aluminium atomic ratio and monoclinic symmetry as a result of the successive steam treatment and aluminium removal. After the aluminium removal step, the crystalline silicate may be ion exchanged with ammonium ions. It is known in the art that such MFI-type crystalline silicates exhibiting orthorhombic symmetry are in the space group Pnma. The X-ray diffraction diagram of such an orthorhombic structure has one peak at d=around 0.365 nm, d=around 0.305 nm and d=around 0.300 nm (see EP0146524).

The starting crystalline silicate has a silicon/aluminium atomic ratio lower than 80. A typical ZSM-5 catalyst has 3.08 wt. % $Al_2O_3$, 0.062 wt. % $Na_2O$ based on the total weight of said ZSM-5 catalyst, and is 100% orthorhombic. Such a catalyst has a silicon/aluminium atomic ratio of 26.9.

The steaming step is carried out as explained above. The steaming tends to reduce the amount of tetrahedral aluminium in the crystalline silicate framework by forming alumina. The aluminium leaching or extraction step is carried out as explained above. In the aluminium leaching step, the crystalline silicate is immersed in the acidic solution or a solution containing the complexing agent and is then preferably heated, for example heated at reflux conditions (at boiling temperature with total return of condensed vapours), for an extended period of time, for example 18 hours. Following the aluminium leaching step, the crystalline silicate is subsequently washed, for example with distilled water, and then dried, preferably at an elevated temperature, for example around 110° C. Optionally, the crystalline silicate is subjected to ion exchange with ammonium ions, for example by immersing the crystalline silicate in an aqueous solution of $NH_4Cl$.

Finally, the catalyst is calcined at an elevated temperature, for example at a temperature of at least 400° C. The calcination period is typically around 3 hours.

The resultant crystalline silicate has monoclinic symmetry, being in the space group $P2_1/n$. The x-ray diffraction diagram of the monoclinic structure exhibits three doublets at d=around 0.36, 0.31 and 0.19 nm. The presence of such doublets is unique for monoclinic symmetry. More particularly, the doublet at d=around 0.36, comprises two peaks, one at d=0.362 nm and one at d=0.365 nm. In contrast, the orthorhombic structure has a single peak at d=0.365 nm.

The presence of a monoclinic structure can be quantified by comparing the X-ray diffraction line intensity at d=around 0.36 nm. When mixtures of MFI crystalline silicates with pure orthorhombic and pure monoclinic structure are prepared, the composition of the mixtures can be expressed as a monoclinicity index (in %). The X-ray diffraction patterns are recorded and the peak height at d=0.362 nm for monoclinicity and d=0.365 nm for orthorhombicity is measured and are denoted as $l_m$ and $l_o$ respectively. A linear regression line between the monoclinicity index and the $l_m/l_o$ gives the relation needed to measure the monoclinicity of unknown samples. Thus the monoclinicity index %=$(axl_m/l_o-b) \times 100$, where a and b are regression parameters.

The such monoclinic crystalline silicate can be produced having a relatively high silicon/aluminium atomic ratio of at least 100, preferably greater than about 200 preferentially without using an organic template molecule during the crystallisation step. Furthermore, the crystallite size of the monoclinic crystalline silicate can be kept relatively low, typically less than 1 micron, more typically around 0.5 microns, since the starting crystalline silicate has low crystallite size which is not increased by the subsequent process steps. Accordingly, since the crystallite size can be kept relatively small, this can yield a corresponding increase in the activity of the catalyst. This is an advantage over known monoclinic crystalline silicate catalysts where typically the crystallite size is greater than 1 micron as they are produced in presence of an organic template molecule and directly having a high Si/Al ratio which inherently results in larger crystallites sizes.

As regards the one or more phosphorus modified zeolites as a catalyst, they can be prepared based on MFI, MOR, MEL, HEU or FER crystalline aluminosilicate molecular sieves having an initial Si/Al ratio advantageously between 4 and 500. The P-modified zeolites of this recipe can be obtained based on cheap crystalline silicates with low Si/Al ratio (below 30).

By way of example said P-modified zeolite is made by a process comprising in that order:
- selecting a zeolite (advantageously with Si/Al ratio between 4 and 500) among $H^+$ or $NH_4^+$-form of MFI, MEL, FER, MOR, HEU;
- introducing P at conditions effective to introduce advantageously at least 0.05 wt. % of P based on the total weigh of the selected zeolite;
- separation of the solid from the liquid if any;
- an optional washing step or an optional drying step or an optional drying step followed by a washing step;
- a calcination step.

The zeolite with low Si/Al ratio has been made previously with or without direct addition of an organic template.

Optionally the process to make said P-modified zeolite comprises the step of steaming, preferably followed by the step of leaching. The method consists in steaming followed by leaching. It is generally known by the persons in the art that steaming of zeolites, results in aluminium that leaves the zeolite framework and resides as aluminiumoxides in and outside the pores of the zeolite. This transformation is known as dealumination of zeolites. The treatment of the steamed zeolite with an acid solution results in dissolution of the extra-framework aluminiumoxides. This transformation is known as leaching. Then the zeolite is separated, advantageously by filtration, and optionally washed. A drying step can be envisaged between filtering and washing steps. The solution after the washing can be either separated, by way of example, by filtering from the solid or evaporated.

Phosphorus can be introduced by any means or, by way of example, according to the recipe described in U.S. Pat. Nos. 3,911,041, 5,573,990 and 6,797,851.

The catalyst made of a P-modified zeolite can be the P-modified zeolite itself or it can be the P-modified zeolite formulated into a catalyst by combining with other materials that provide additional hardness or catalytic activity to the finished catalyst product.

The separation of the liquid from the solid is advantageously made by filtering at a temperature between 0-90° C., centrifugation at a temperature between 0-90° C., evaporation or equivalent.

Optionally, the zeolite can be dried after separation before washing. Advantageously said drying is made at a temperature between 40-600° C., and/or advantageously for 1-10 h. This drying can be processed either in a static condition or in a gas flow. Air, nitrogen or any inert gases can be used.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering.

Final calcination step is performed advantageously at the temperature 400-700° C. either in a static condition or in a gas flow. Air, nitrogen or any inert gases can be used.

According to a specific embodiment the phosphorous modified zeolite is made by a process comprising in that order:
- selecting a zeolite (advantageously with Si/Al ratio between 4 and 500, from 4 to 30 in a specific embodiment) among $H^+$ or $NH_4^+$-form of MFI, MEL, FER, MOR, HEU;
- steaming at a temperature ranging from 400 to 870° C. and/or for a period ranging between 0.01 h and 200 h;
- leaching with an aqueous acid solution at conditions effective to remove a substantial part of Al from the zeolite;
- introducing P with an aqueous solution containing the source of P at conditions effective to introduce advantageously at least 0.05 wt. % of P based on the total weight of the selected zeolite;
- separation of the solid from the liquid;
- an optional washing step or an optional drying step or an optional drying step followed by a washing step;
- a calcination step.

Optionally between the steaming step and the leaching step there is an intermediate step such as, by way of example, contact with silica powder and drying.

Advantageously the selected MFI, MEL, FER, MOR, HEU (or $H^+$ or $NH_4^+$-form MFI, MEL, FER, MOR, HEU) has an initial atomic ratio Si/Al of 100 or lower and from 4 to 30 in a specific embodiment. The conversion to the $H^+$ or $NH_4^+$-form is known per se and is described in U.S. Pat. Nos. 3,911,041 and 5,573,990.

Advantageously the final P-content is at least 0.05 wt. % based on the total weight of the phosphorus-modified zeolites and preferably between 0.3 wt. % and 7 w. %. Advantageously, the phosphorus-modified zeolites comprise at least 10% of Al in less in respect to parent zeolite MFI, MEL, FER, MOR and HEU since it has been extracted and removed from the zeolite by the leaching.

Then the zeolite either is separated from the washing solution or is dried without separation from the washing solution. Said separation is advantageously made by filtration. Then the zeolite is calcined, by way of example, at 400° C. for 2-10 hours.

In the steaming step, the temperature is preferably from 420 to 870° C., more preferably from 480 to 760° C. The pressure is preferably atmospheric pressure and/or the water partial pressure may range from 13 to 100 kPa. The steam atmosphere preferably contains from 5 to 100 vol. % steam along with from 0 to 95 vol. % of an inert gas based on the total volume of the steam atmosphere. For example, the inert gas is nitrogen. The steaming is preferably carried out for a period of from 0.01 to 200 hours, advantageously from 0.05 to 200 hours, more preferably from 0.05 to 50 hours. The steaming tends to reduce the amount of tetrahedral aluminium in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g. the sodium or ammonium salts) or a mixture of two or more of such acids or salts.

The residual P-content is adjusted by P-concentration in the aqueous acid solution containing the source of P, drying conditions and a washing procedure if any. A drying step can be envisaged between filtering and washing steps.

Said phosphorus-modified zeolite can be used as catalyst itself. In another embodiment it can be formulated into a catalyst by combining with other materials that provide additional hardness or catalytic activity to the finished catalyst product. Materials which can be blended with the P-modified zeolite can be various inert or catalytically active materials, or various binder materials. These materials include compositions such as kaolin and other clays, various forms of rare earth metals, phosphates, alumina or alumina sol, titania, zirconia, quartz, silica or silica sol, and mixtures thereof. These components are effective in densifying the catalyst and increasing the strength of the formulated catalyst. The catalyst may be formulated into sphere or formed into a spray-dried particles. The amount of P-modified zeolite which is contained in the final catalyst product ranges from 10 to 90 weight percent of the total catalyst, preferably 20 to 70 weight percent of the total catalyst.

The Bed Comprising Particles—Conductive Particles

To achieve the required temperature necessary to carry out the catalytic dehydration of the one or more alcohols into one or more olefins, at least 10 wt. % of the particles based on the total weight of the particles of the bed are electrically conductive, have a resistivity ranging from 0.001 Ohm·cm to 500 Ohm·cm at 400° C.

For example, the electrically particles of the bed are or comprise one or more selected from one or more metallic alloys, one or more non-metallic resistors, one or more metallic carbides, one or more metallic nitrides, one or more metallic phosphides, one or more carbon-containing particles, one or more superionic conductors, one or more phosphate electrolytes, and any mixture thereof.

For example, from 50 wt. % to 100 wt. % of the electrically conductive particles of the bed based on the total weight of the electrically conductive particles of the bed are one or more selected from one or more metallic alloys, one or more non-metallic resistors, one or more metallic carbides, one or more metallic nitrides, one or more metallic phosphides, one or more carbon-containing particles, one or more superionic conductors, one or more phosphate electrolytes, and any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

In an embodiment, from 50 wt. % to 100 wt. % of the electrically conductive particles of the bed based on the total weight of the electrically conductive particles of the bed are devoid of graphite and/or carbon black; preferably, from 60 wt. % to 95 wt. %; more preferably from 70 wt. % to 90 wt. %; and even more preferably from 75 wt. % to 85 wt. %.

For example, the content of electrically conductive particles is ranging from 10 wt. % to 100 wt. % based on the total weight of the particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the content of electrically conductive particles based on the total weight of the bed is at least 12 wt. % based on the total weight of the particles of the bed; preferably, at least 15 wt. %, more preferably, at least 20 wt. %; even more preferably at least 25 wt. %, and most preferably at least 30 wt. % or at least 40 wt. % or at least 50 wt. % or at least 60 wt. %.

For example, the electrically conductive particles have a resistivity ranging from 0.005 to 400 Ohm·cm at 400° C., preferably ranging from 0.01 to 300 Ohm·cm at 400° C.; more preferably ranging from 0.05 to 150 Ohm·cm at 400° C. and most preferably ranging from 0.1 to 100 Ohm·cm at 400° C.

For example, the electrically conductive particles have a resistivity of at least 0.005 Ohm·cm at 400° C.; preferably of at least 0.01 Ohm·cm at 400° C., more preferably of at least 0.05 Ohm·cm at 400° C.; even more preferably of at least 0.1 Ohm·cm at 400° C., and most preferably of at least 0.5 Ohm·cm at 400° C.

For example, the electrically conductive particles have a resistivity of at most 400 Ohm·cm at 400° C.; preferably of at most 300 Ohm·cm at 400° C., more preferably of at most 200 Ohm·cm at 400° C.; even more preferably of at most 150 Ohm·cm at 400° C., and most preferably of at most 100 Ohm·cm at 400° C.

For example, the particles of the bed have an average particle size ranging from 5 to 300 μm as determined by sieving according to ASTM D4513-11, preferably ranging from 10 to 200 μm and more preferably ranging from 30 to 150 μm.

For example, the electrically conductive particles of the bed have an average particle size ranging from 5 to 300 μm as determined by sieving according to ASTM D4513-11, preferably ranging from 10 to 200 μm and more preferably ranging from 30 to 150 μm.

The electrical resistance is measured by a four-probe DC method using an ohmmeter. A densified power sample is shaped in a cylindrical pellet that is placed between the probe electrodes. Resistivity is determined from the measured resistance value, R, by applying the known expression $\rho = R \times A/L$, where L is the distance between the probe electrodes typically a few millimetres and A the electrode area.

The electrically conductive particles of the bed can exhibit electronic, ionic or mixed electronic-ionic conductivity. The ionic bonding of many refractory compounds allows for ionic diffusion and correspondingly, under the influence of an electric field and appropriate temperature conditions, ionic conduction.

The electrical conductivity, σ, the proportionality constant between the current density j and the electric field E, is given by $$\sigma = j/E = \Sigma c_i \times Z_i q \times \mu_i$$

where $c_i$ is the carrier density (number/cm$^3$), $\mu_i$ the mobility (cm$^2$/Vs), and $Z^i q$ the charge (q=1.6×10$^{-19}$ C) of the ith charge carrier. The many orders of magnitude differences in σ between metals, semiconductors and insulators generally result from differences in c rather than μ. On the other hand, the higher conductivities of electronic versus ionic conductors are generally due to the much higher mobilities of electronic versus ionic species.

The most common materials that can be used for resistive heating is subdivided into nine groups:

(1) Metallic alloys for temperatures up to 1200-1400° C.,
(2) non-metallic resistors like silicon carbide (SiC), molybdenum disilicide (MoSi$_2$), nickel silicide (NiSi), sodium silicide (Na$_2$Si), magnesium silicide (Mg$_2$Si), platinum silicide (PtSi), titanium silicide (TiSi$_2$) and tungsten silicide (WSi$_2$) up to 1600-1900° C.,
(3) carbon-containing materials,
(4) metallic carbides,
(5) metallic nitrides,
(6) metallic phosphides,
(7) superionic conductors, and
(8) phosphate electrolytes.

A first group of metallic alloys, for temperatures up to 1150-1250° C., can be constituted by Ni—Cr alloys with low Fe content (0.5-2.0%), preferably alloy Ni—Cr (80% Ni, 20% Cr) and (70% Ni, 30% Cr). Increasing the content of Cr increases the material resistance to oxidation at high temperatures. A second group of metallic alloys having three components are Fe—Ni—Cr alloys, with maximum operating temperature in an oxidizing atmosphere to 1050-1150°

C. but which can be conveniently used in reducing atmospheres or Fe—Cr—Al (chemical composition 15-30% Cr, 2-6% Al and Fe balance) protecting against corrosion by a surface layer of oxides of Cr and Al, in oxidizing atmospheres can be used up to 1300-1400° C. Silicon carbide as non-metallic resistor can exhibit wide ranges of resistivity that can be controlled by the way they are synthesized and the presence of impurities like aluminium, iron, oxide, nitrogen or extra carbon or silicon resulting in non-stoichiometric silicon carbide. In general silicon carbide has a high resistivity at low temperature but has good resistivity in the range of 500 to 1200° C. In an alternative embodiment, the non-metallic resistor can be devoid of silicon carbide, and/or can comprise molybdenum disilicide ($MoSi_2$), nickel silicide (NiSi), sodium silicide ($Na_2Si$), magnesium silicide ($Mg_2Si$), platinum silicide (PtSi), titanium silicide ($TiSi_2$), tungsten silicide ($WSi_2$) or a mixture thereof.

Several sublattice disordered oxides or sulphides have high ion transport ability at increasing temperature. These are superionic conductors, such as $LiAlSiO_4$, $Li_{10}GeP_2S_{12}$, $Li_{3.6}Si_{0.6}P_{0.4}O_4$, NaSICON (sodium (Na) Super Ionic CONductor) with the general formula $Na_{1+x}Zr_2P_{3-x}Si_xO_{12}$ with $0<x<3$, for example $Na_3Zr_2PSi_2O_{12}$ (x=2), or sodium beta alumina, such as $NaAl_{11}O_{17}$, $Na_{1.6}Al_{11}O_{17.3}$, and/or $Na_{1.76}Li_{0.38}Al_{10.62}O_{17}$.

Phosphate electrolytes such as $LiPO_4$ or $LaPO_4$ can also be used as electrically conductive particles.

Metallic carbides, metallic nitrides and metallic phosphides can also be selected as electrically conductive particles. For example, metallic carbides are selected from iron carbide ($Fe_3C$), molybdenum carbide (such as a mixture of MoC and $Mo_2C$). For example, said one or more transition metal nitrides are selected from zirconium nitride (ZrN), tungsten nitride (such as a mixture of $W_2N$, WN, and $WN_2$), vanadium nitride (VN), tantalum nitride (TaN), and/or niobium nitride (NbN). For example, said one or more metallic phosphides are selected from copper phosphide ($Cu_3P$), indium phosphide (InP), gallium phosphide (GaP), sodium phosphide $Na_3P$), aluminium phosphide (AlP), zinc phosphide ($Zn_3P_2$) and/or calcium phosphide ($Ca_3P_2$).

It is a preferred embodiment of the present disclosure, the electrically conductive particles that exhibit only sufficiently low resistivity at a high temperature can be heated by external means before reaching the high enough temperature where resistive heating with electricity overtakes or can be mixed with a sufficiently low resistivity solid at a low temperature so that the resulting resistivity of the mixture allows to heat the fluidized bed to the desired reaction temperature.

For example, the electrically conductive particles of the bed are or comprise silicon carbide. For example, at least 10 wt. % of the electrically conductive particles based on the total weight of the electrically conductive particles of the bed are silicon carbide particles and have a resistivity ranging from 0.001 Ohm·cm to 500 Ohm·cm at of 400° C.

In the embodiment wherein the electrically conductive particles of the bed are or comprise silicon carbide, the person skilled in the art will have the advantage to conduct a step of pre-heating with a gaseous stream said fluidized bed reactor before conduct said endothermic reaction in the fluidized bed reactor. Advantageously, the gaseous stream is a stream of inert gas, i.e., nitrogen, argon, helium, methane, hydrogen or steam. The temperature of the gaseous stream can be at least 300° C., or at least 350° C., or at least 400° C., or at least 450° C., and/or at most 500° C. Advantageously, the temperature of the gaseous stream can be comprised between 300° C. and 500° C. Said gaseous stream of inert gas can also be used as the fluidification gas. The pre-heating of the said gaseous stream of inert gas is performed thanks to conventional means, including using electrical energy. The temperature of the gaseous stream used for the preheating of the bed doesn't need to reach the temperature reaction.

Indeed, the resistivity of silicon carbide at ambient temperature is high, to ease the starting of the reaction, it may be useful to heat the fluidized bed by external means, as with preference the fluidized bed reactor is devoid of heating means. Once the bed is heated at the desired temperature, the use of a hot gaseous stream may not be necessary.

However, in an embodiment, the electrically conductive particles of the bed are or comprise a mixture of silicon carbide particles and electrically conductive particles different from silicon carbide particles.

The pre-heating step may be also used in the case wherein electrically conductive particles different from silicon carbide particles are present in the bed. For example, it may be used when the content of silicon carbide in the electrically conductive particles of the bed is more than 80 wt. % based on the total weight of the particles of the bed, for example, more than 85 wt. %, for example, more than 90 wt. %, for example, more than 95 wt. %, for example, more than 98 wt. %, for example, more than 99 wt. %. However, a pre-heating step may be used whatever is the content of silicon carbide particles in the bed.

In the embodiment wherein the electrically conductive particles of the bed are or comprise a mixture of silicon carbide particles and electrically conductive particles different from silicon carbide particles, the electrically conductive particles of the bed may comprise from 10 wt. % to 99 wt. % of silicon carbide particles based on the total weight of the electrically conductive particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the electrically conductive particles of the bed are or comprise a mixture of silicon carbide particles and electrically conductive particles different from silicon carbide particles and the electrically conductive particles of the bed comprises at least 40 wt. % of silicon carbide particles based on the total weight of the electrically conductive particles of the bed; preferably at least 50 wt. %, more preferably at least 60 wt. %, even more preferably at least 70 wt. % and most preferably at least 80 wt. %.

In an embodiment, the electrically conductive particles of the bed may comprise from 10 wt. % to 90 wt. % of electrically conductive particles different from silicon carbide particles based on the total weight of the electrically conductive particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

However, it may be interesting to keep the content of electrically conductive particles different from silicon carbide particles quite low in the mixture. Thus, in an embodiment, the electrically conductive particles of the bed are or comprise a mixture of silicon carbide particles and electrically conductive particles different from silicon carbide particles and electrically conductive particles of the bed comprises from 1 wt. % to 20 wt. % of electrically conductive particles different from silicon carbide based on the total weight of the electrically conductive particles of the bed; preferably, from 2 wt. % to 15 wt. %, more preferably, from 3 wt. % to 10 wt. %, and even more preferably, from 4 wt. % to 8 wt. %.

For example, the electrically conductive particles of the bed are or comprise a mixture of silicon carbide particles and particles different from silicon carbide particles and the said particles different from silicon carbide particles are or comprise molybdenum disilicide particles.

Thus, in an embodiment, the electrically conductive particles are a combination of silicon carbide particles and molybdenum disilicide particles. Such electrically conductive particles, upon the electrification of the fluidized bed reactor, will heat up and because of their fluidification, will contribute to the raise and/or to the maintaining of the temperature within the reactor. The Joule heating of molybdenum disilicide allows accelerating the heating of the reactant and/or of the other particles that are present within the fluidized bed reactor.

It is also preferable that the molybdenum disilicide has an average particle size ranging from 1 to 400 μm as determined by sieving according to ASTM D4513-11, preferably from 5 to 300 μm, more preferably ranging from 10 to 200 μm and most preferably ranging from 30 to 150 μm.

The presence of molybdenum disilicide particles in the bed allows applying the process according to the disclosure with or without the pre-heating step, preferably without the pre-heating step. Indeed, the molybdenum disilicide particles, upon the electrification of the fluidized bed reactor, will heat up and because of their fluidification, will contribute to raising and/or maintaining the desired temperature within the reactor.

The Silicon Carbide Particles

For example, the silicon carbide is selected from sintered silicon carbide, nitride-bounded silicon carbide, recrystallised silicon carbide, reaction bonded silicon carbide and any mixture thereof.

Sintered SiC (SSiC) is a self-bonded material containing a sintering aid (typically boron) of less than 1% by weight.

Recrystallized silicon carbide (RSiC), a high purity SiC material sintered by the process of evaporation-condensation without any additives.

Nitride-bonded silicon carbide (NBSC) is made by adding fine silicon powder with silicon carbide particles or eventually in the presence of a mineral additive and sintering in a nitrogen furnace. The silicon carbide is bonded by the silicon nitride phase ($Si_3N_4$) formed during nitriding.

Reaction bonded silicon carbide (RBSC), also known as siliconized silicon carbide or SiSiC, is a type of silicon carbide that is manufactured by a chemical reaction between porous carbon or graphite with molten silicon. The silicon reacts with the carbon forming silicon carbide and bonds the silicon carbide particles. Any excess silicon fills the remaining pores in the body and produces a dense SiC—Si composite. Due to the left-over traces of silicon, reaction bonded silicon carbide is often referred to as siliconized silicon carbide. The process is known variously as reaction bonding, reaction sintering, self-bonding, or melt infiltration.

In general, high purity SiC particles have resistivity above 1000 Ohm·cm, whereas sintered, reaction bonded and nitride-bonded can exhibit resistivities of about 100 to 1000 depending on the impurities in the SiC phase. Electrical resistivity of bulk polycrystalline SiC ceramics shows a wide range of resistivity depending on the sintering additive and heat-treatment conditions (Journal of the European Ceramic Society, Volume 35, Issue 15, December 2015, Pages 4137; Ceramics International, Volume 46, Issue 4, March 2020, Pages 5454). SiC polytypes with high purity possess high electrical resistivity ($>10^6$ Ω·cm) because of their large bandgap energies. However, the electrical resistivity of SiC is affected by doping impurities. N and P act as n-type dopants and decrease the resistivity of SiC, whereas Al, B, Ga, and Sc act as p-type dopants. SiC doped with Be, O, and V are highly insulating. N is considered the most efficient dopant for improving the electrical conductivity of SiC. For N doping of SiC (to decrease resistivity) $Y_2O_3$ and $Y_2O_3$-$REM_2O_3$ (REM, rare earth metal=Sm, Gd, Lu) have been used as sintering additives for efficient growth of conductive SiC grains containing N donors. N-doping in SiC grains was promoted by the addition of nitrides (AlN, BN, $Si_3N_4$, TiN, and ZrN) or combinations of nitrides and $Re_2O_3$ (AlN-$REM_2O_3$ (REM=Sc, Nd, Eu, Gd, Ho, and Er) or TiN—$Y_2O_3$).

The Installation

The terms "bottom" and "top" are to be understood in relation to the general orientation of the installation or the fluidized bed reactor. Thus, "bottom" will mean greater ground proximity than "top" along the vertical axis. In the different figures, the same references designate identical or similar elements.

FIG. 1 illustrates a prior art fluidized bed reactor 1 comprising a reactor vessel 3, a bottom fluid nozzle 5 for the introduction of a fluidizing gas and an alcohol-containing feedstock, an optional inlet 7 for the material loading, an optional outlet 9 for the material discharge and a gas outlet 11 and a bed 15. In the fluidized bed reactor 1 of FIG. 1 the heat is provided by preheating the feedstock by combustion of fossil fuels using heating means 17 arranged for example at the level of the line that provides the reactor with the fluidizing gas and the alcohol-containing feedstock.

The installation of the present disclosure is now described with reference to FIGS. 2 to 5. For sake of simplicity, internal devices are known by the person in the art that are used in fluidized bed reactors, like bubble breakers, deflectors, particle termination devices, cyclones, ceramic wall coatings, thermocouples, etc. . . . are not shown in the illustrations.

Figure 2:
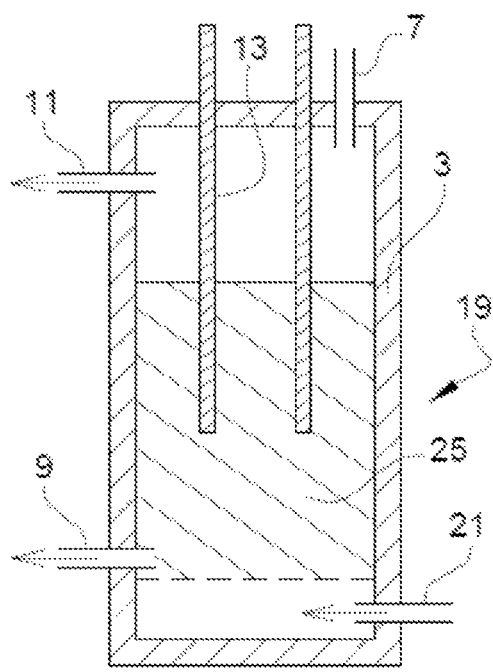
FIG. 2 illustrates an installation according to the disclosure with one reactor wherein the heating zone and reaction zone are the same.

FIG. 2 illustrates a first installation with a fluidized bed reactor 19 where the heating and reaction zone are the same. The fluidized bed reactor 19 comprises a reactor vessel 3, a bottom fluid nozzle 21 for the introduction of a fluidizing gas and an alcohol-containing feedstock, an optional inlet 7 for the material loading, an optional outlet 9 for the material discharge and a gas outlet 11. The fluidized bed reactor 1 of FIG. 19 shows two electrodes 13 submerged in bed 25.

Figure 3:
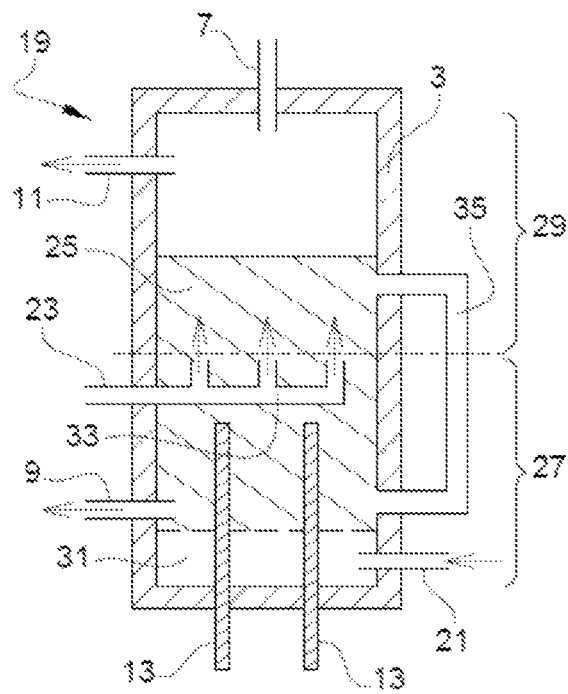
FIG. 3 illustrates an installation according to the disclosure with one reactor wherein the heating zone and reaction zone are arranged one above the other.

FIG. 3 illustrates an embodiment wherein at least one fluidized bed reactor 19 comprises a heating zone 27 and a reaction zone 29 with the heating zone 27 is the bottom zone and the reaction zone 29 is on top of the heating zone 27. One or more fluid nozzles 23 to provide an alcohol-containing feedstock to the reaction zone from a distributor 33. As it can be seen in FIG. 3, the one or more fluid nozzles 23 can be connected to a distributor 33 to distribute the alcohol-containing feedstock inside the bed 25.

Figure 4:
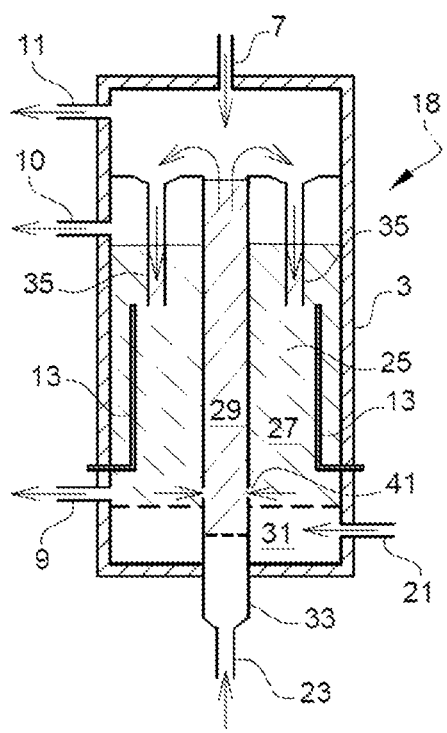
FIG. 4 illustrates an installation according to the disclosure with one reactor wherein the heating zone and reaction zone are arranged one lateral to the other.

FIG. 4 illustrates an installation wherein at least one fluidized bed reactor 18 comprises at least two lateral zones with the outer zone being the heating zone 27 and the inner zone being the reaction zone 29. The heated particles of the bed 25 from the outer zone are transferred to the inner zone by one or more openings 41 and mixed with the alcohol-containing feedstock and/or steam. At the end of the reaction zone the particles are separated from the reaction product and transferred to the heating zone.

Figure 5:
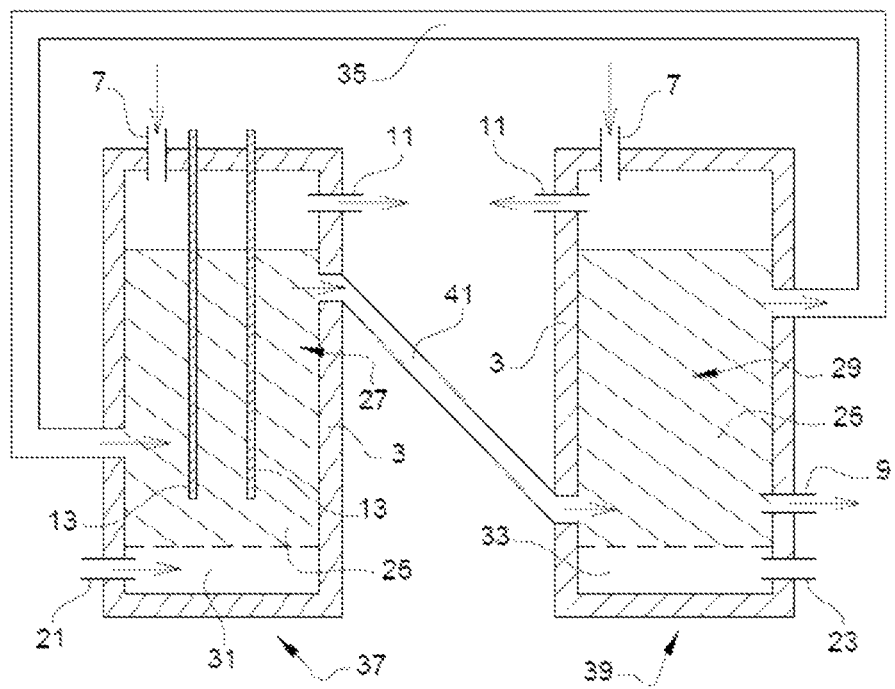
FIG. 5 illustrates an installation according to the disclosure with two reactors.

FIG. 5 illustrates the installation that comprises at least two fluidized bed reactors (37, 39) connected one to each other wherein at least one fluidized bed reactor is the heating zone 27 and one at least one fluidized bed reactor is the reaction zone 29.

The present disclosure provides for an installation to be used in a process to perform an endothermic catalytic dehydration of one or more alcohols having at least two carbon atoms into one or more olefins, said installation comprises at least one fluidized bed reactor (18, 19, 37, 39) comprising:
- at least two electrodes 13,
- a reactor vessel 3;
- one or more fluid nozzles (21, 23) for the introduction of a fluidizing gas and/or of an alcohol-containing feedstock comprising one or more alcohols having at least two carbon atoms and optionally one or more inert gases and/or one or more diluent gases within at least one fluidized bed reactor (18, 19, 37, 39); and
- a bed 25 comprising particles;

wherein the particles of the bed 25 comprise electrically conductive particles and particles of a catalytic composition, wherein at least 10 wt. % of the particles of the bed based on the total weight of the particles of the bed 25 are electrically conductive, have a resistivity ranging from 0.001 Ohm·cm to 500 Ohm·cm at 400° C., and wherein the catalytic composition comprises one or more solid acid catalysts.

In particular, the disclosure provides an installation to perform an endothermic catalytic dehydration of one or more alcohols having at least two carbon atoms into one or more olefins, said installation comprises
i) an electrified fluidized bed unit with at least one fluidized bed reactor (18, 19, 37, 39) comprising:
   - at least two electrodes (13);
   - a reactor vessel (3);
   - one or more fluid nozzles (21, 23) for the introduction of an alcohol-containing feedstock comprising one or more alcohols having at least two carbon atoms and optionally one or more inert gases and/or one or more diluent gases within at least one fluidized bed reactor (18, 19, 37, 39); and
   - a bed (25) comprising particles;
ii) a product-recovery unit;
(iii) an olefin-transformation unit, wherein said olefin-transformation unit is selected from an olefin oligomerization unit or an aromatic alkylation unit or an olefin oligomerization and aromatic alkylation unit,
wherein the product-recovery is downstream the electrified fluidized bed unit and upstream the olefin-transformation unit;
the installation is remarkable in that the particles of the bed comprise electrically conductive particles and particles of a catalytic composition, wherein at least 10 wt. % of the particles of the bed based on the total weight of the particle of the bed are electrically conductive, have a resistivity ranging from 0.001 Ohm·cm to 500 Ohm·cm at a temperature of 400° C., and wherein the catalytic composition comprises one or more solid acid catalysts.

With preference, the at least two electrodes comprise or are made of tantalum.

Details regarding the oligomerization step (e) that can be carried out on the one or more olefins recovered at step (d) and that is to be carried out in an olefin-transformation unit being an olefin oligomerisation unit are to be found in the review entitled "*Applications of light olefin oligomerization to the production of fuels and chemicals*" (Nicholas C. P., *Applied Catal. A: General*, 2017, 543, 82-97) and/or in chapter 10 (p. 271) of the book entitled "Hydrocarbon Biorefinery" (ISBN 978-0-12-823306-1).

Details regarding the alkylation step (f) of aromatic compounds that can be carried out on the one or more olefins recovered at step (d) and that is to be carried out in an olefin-transformation unit being an aromatic alkylation unit are to be found in the review entitled "*Alkylation of aromatics with ethylene and propylene: recent developments in commercial processes*" (Degnan Jr. T. F., et al., *Applied Catal. A: General*, 2001, 221, 283-294) and/or in the review entitled "*Recent advances in the industrial alkylation of aromatics: new catalysts and new processes*" (Perego C., et al., *Catal. Today*, 2002, 73, 3-22).

The aromatic alkylation unit is designed to receive in addition of the one or more olefins recovered at step (d) a source of one or more aromatic compounds that are provided upon step (f). Advantageously, the oligomerisation step (e) on the one or more olefins recovered at step (d) and the alkylation step (g) of one or more aromatic compounds provided at step (f) can occur simultaneously, for example within the same olefin-transformation unit being an olefin oligomerization and an aromatic alkylation unit.

Upon transformation of the olefins into the olefin oligomerization unit or into the aromatic alkylation unit or into an olefin oligomerization and aromatic alkylation unit, and if there are remaining olefinic bonds, it is useful to hydrogenate them, especially upon achievement of the oligomerisation step (e) which generates compounds bearing olefinic moieties. That is the reason why an optional hydrogenation unit can be disposed downstream of the olefin-transformation unit.

For example, the electrically conductive particles of the bed are or comprise one or more selected from one or more metallic alloys, one or more non-metallic resistors, one or more metallic carbides, one or more metallic nitrides, one or more metallic phosphides, one or more carbon-containing particles, one or more superionic conductors, one or more phosphate electrolytes, and any mixture thereof.

In an embodiment, from 50 wt. % to 100 wt. % of the electrically conductive particles of the bed based on the total weight of the electrically conductive particles of the bed are one or more selected from one or more metallic alloys, one or more non-metallic resistors, one or more metallic carbides, one or more metallic nitrides, one or more metallic phosphides, one or more carbon-containing particles, one or more superionic conductors, one or more phosphate electrolytes, and any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, one electrode is a submerged central electrode or two electrodes 13 are submerged within the reactor vessel 3 of at least one reactor (18, 19, 37).

For example, the fluidizing gas is one or more diluent gases.

In a preferred embodiment, the at least one fluidized bed reactor (18, 19, 37, 39) is devoid of heating means. For example, at least one fluidized bed reactor is devoid of heating means selected from ovens, gas burners, hot plates, or any combination thereof. For example, all the fluidized bed reactors are devoid of heating means selected from ovens, gas burners, hot plates, or any combination thereof. In a preferred embodiment, the at least one fluidized bed reactor comprising at least two electrodes and a bed comprising particles is devoid of packing.

For example, the reactor vessel 3 has an inner diameter of at least 100 cm, or at least 200 cm; or at least 400 cm. Such a large diameter allows to carry out the chemical reaction at an industrial scale, for example at a weight hourly space velocity of said reaction stream comprised between 0.1 h$^{-1}$ and 100 h$^{-1}$, preferably comprised between 1.0 h$^{-1}$ and 50 h$^{-1}$, more preferably comprised between 1.5 h$^{-1}$ and 10 h$^{-1}$, even more preferably comprised between 2.0 h$^{-1}$ and 6.0 h$^{-1}$. The weight hourly space velocity is defined as the ratio of mass flow of the reaction stream to the mass of solid particulate material in the fluidized bed.

The at least one fluidized bed reactor (18, 19, 37) comprises at least two electrodes 13. For example, one electrode is in electrical connection with the outer wall of the fluidized bed reactor, while one additional electrode is submerged into the fluidized bed 25, or both electrodes 13 are submerged into the fluidized bed 25. Said at least two electrodes 13 are electrically connected and can be connected to a power supply (not shown).

For example, the at least one fluidized bed reactor comprises at least one cooling device arranged to cool at least one electrode.

During use of the fluidized bed reactor, an electric potential of at most 300 V is applied, preferably at most 250 V, more preferably at most 200 V, even more preferably at most 150 V, most preferably at most 100 V, even most preferably at most 90 V, or at most 80 V.

Thanks to the fact that the power of the electric current can be tuned, it is easy to adjust the temperature within the reactor bed.

With preference, the reactor vessel 3 comprises a reactor wall made of materials that are corrosion-resistant materials and advantageously said reactor wall materials comprise nickel (Ni), SiAlON ceramics, yttria-stabilized zirconia (YSZ), tetragonal polycrystalline zirconia (TZP) and/or tetragonal zirconia polycrystal (TPZ). SiAlON ceramics are ceramics based on the elements silicon (Si), aluminium (Al), oxygen (O) and nitrogen (N). They are solid solutions of silicon nitride ($Si_3N_4$), where Si—N bonds are partly replaced with Al—N and Al—O bonds.

For example, the reactor vessel 3 is made of an electro-resistive material that is a mixture of silicon carbide and molybdenum disilicide; and the electro-resistive material of the reactor vessel 3 comprises from 10 wt. % to 99 wt. % of silicon carbide based on the total weight of the electro-resistive material; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the reactor vessel 3 is made of an electro-resistive material that is a mixture of silicon carbide and molybdenum disilicide.

For example, the reactor vessel 3 is not conductive. For example, the reactor vessel 3 is made of ceramic.

For example, the at least one fluidized bed reactor (18, 19, 37, 39) comprises a heating zone 27 and a reaction zone 29, one or more fluid nozzles 21 to provide a fluidizing gas to at least the heating zone from a distributor 31, one or more fluid nozzles 23 to provide an alcohol-containing feedstock to the reaction zone from a distributor 33, and means 41 to transport the particles from the heating zone 27 to the reaction zone 29 when necessary, and optional means 35 to transport the particles from the reaction zone 29 back to the heating zone 27.

For example, as illustrated in FIG. 3, the at least one fluidized bed reactor is a single one fluidized bed reactor 19 wherein the heating zone 27 is the bottom part of the fluidized bed reactor 19 while the reaction zone 29 is the top part of the fluidised bed reactor 19; with preference, the installation comprises one or more fluid nozzles 23 to inject an alcohol-containing feedstock between the two zones (27, 29) or in the reaction zone 29. The fluidized bed reactor 19 further comprises optionally an inlet 7 for the material loading, optionally an outlet 9 for the material discharge and a gas outlet 11. With preference, the fluidized bed reactor 19 is devoid of heating means. For example, the electrodes 13 are arranged at the bottom part of the fluidized bed reactor 19, i.e., in the heating zone 27. For example, the top part of the fluidised bed reactor 19, i.e., the reaction zone 29, is devoid of electrodes. Optionally, the fluidized bed reactor 19 comprises means 35 to transport the particles from the reaction zone 29 back to the heating zone 27; such as by means of a line arranged between the top part and the bottom part of the fluidized bed reactor 19.

For example, as illustrated in FIG. 4, the installation comprises at least two lateral fluidized bed zones (27, 29) connected one to each other wherein at least one fluidized bed zone 27 is the heating zone and at least one fluidized bed zone 29 is the reaction zone. For example, the heating zone 27 is surrounding the reaction zone 29. With preference, the installation comprises one or more fluid nozzles 23 arranged to inject an alcohol-containing feedstock and/or steam to the at least one reaction zone 29 by means of a distributor 33. The fluidized bed zones (27, 29) further comprise optionally an inlet 7 for the material loading and a gas outlet 11. With preference, the at least one fluidized bed zone being the heating zone 27 and/or the at least one fluidized bed zone being the reaction zone 29 is devoid of heating means. For example, the at least one fluidized bed zone being the reaction zone 29 shows optionally an outlet 9 for the material discharge. One or more fluid nozzles 21 provide a fluidizing gas to at least the heating zone from a distributor 31. With one or more inlet devices 41, heated particles are transported from the heating zone 27 to the reaction zone 29, and with one or more means 35 comprising downcomers, the separated particles are transported from the reaction zone 29 back to the heating zone 27. The fluidization gas for the heating zone 27 can be an inert diluent, like one or more selected from steam, hydrogen, carbon dioxide, methane, argon, helium and nitrogen. In such a configuration the fluidization gas for the heating zone can also comprise air or oxygen to burn deposited coke from the particles.

For example, as illustrated in FIG. 5, the installation comprises at least two fluidized bed reactors (37, 39) connected one to each other wherein at least one fluidized bed reactor 37 is the heating zone 27 and at least one fluidized bed reactor 39 is the reaction zone 29. With preference, the installation comprises one or more fluid nozzles 23 arranged to inject an alcohol-containing feedstock and/or steam to the at least one fluidized bed reactor 39 being the reaction zone 29. The fluidized bed reactors (37, 39) further comprise optionally an inlet 7 for the material loading and a gas outlet 11. With preference, the at least one fluidized bed reactor 37 being the heating zone 27 and/or the at least one fluidized bed reactor 39 being the reaction zone 29 is devoid of heating means. For example, the at least one fluidized bed reactor 39 being the reaction zone 29 shows optionally an outlet 9 for the material discharge. By means of the inlet device 41, heated particles are transported from the heating zone 27 to the reaction zone 29 when necessary, and by means of device 35, the separated particles after the reaction zone are transported from the reaction zone back to the heating zone. The fluidization gas for the heating zone can be an inert diluent, like one or more selected from steam, hydrogen, carbon dioxide, methane, argon, helium, and nitrogen. In such a configuration the fluidization gas for the heating zone can also comprise air or oxygen to burn deposited coke from the particles.

For example, the at least one fluidized bed reactor 37 being the heating zone 27 comprises at least two electrodes 13 whereas the at least one fluidized bed reactor 39 being the reaction zone 29 is devoid of electrodes.

For example, the at least two fluidized bed reactors (37, 39) are connected one to each other by means 41 suitable to transport the particles from the heating zone 27 to the reaction zone 29, such as one or more lines.

For example, the at least two fluidized bed reactors (37, 39) are connected one to each other by means 35 suitable to transport the particles from the reaction zone 29 back to the heating zone 27, such as one or more lines.

The Catalytic Dehydration of One or More Alcohols Having at Least Two Carbon Atoms into One or More Olefins For example, the catalytic dehydration of one or more alcohols having at least two carbon atoms into one or more olefins is conducted at a temperature ranging from 200° C. to 500° C., preferably from 240° C. to 490° C., more preferably from 260° C. to 480° C.

For example, the catalytic dehydration of one or more alcohols having at least two carbon atoms into one or more olefins is performed at a pressure ranging between 0.05 MPa and 3 MPa, preferably between 0.05 MPa and 1.5 MPa, more preferably between 0.12 MPa and 0.8 MPa, or between 0.12 MPa and 0.5 MPa. This pressure is considered as a moderate pressure, easy to achieve and economical.

For example, the partial pressure of the alcohol-containing feedstock is ranging between 0.12 MPa and 0.7 MPa.

For example, said catalytic dehydration of one or more alcohols having at least two carbon atoms into one or more olefins is conducted in presence of a reaction stream and is performed at a weight hourly space velocity of said reaction stream comprised between 0.1 h$^{-1}$ and 100 h$^{-1}$, preferably comprised between 1.0 h$^{-1}$ and 50 h$^{-1}$, more preferably comprised between 1.5 h$^{-1}$ and 10 h$^{-1}$, even more preferably comprised between 2.0 h$^{-1}$ and 6.0 h$^{-1}$.

For example, the residence time of the alcohol-containing feedstock in the fluidised bed section of the reactor where the temperature is between 260° C. and 500° C., may range from 0.1 to 10 seconds or from 1 to 10 seconds.

Test and Determination Method

X-Ray Diffraction (XRD) was used to determine the crystalline structure of the catalyst. It has been carried out on powder samples of the synthetic one or more zeolites and was performed using a PANalytical X'Pert Pro diffractometer with CuKα monochromatized radiation (λ=1.5418 Å, 45 kV, 40 mA). The samples were scanned in the range 5-50° 2θ with a step size of 0.02°. Unit cell parameters of zeolite particles were determined from the X-Ray diffraction data by calculation based on a Le Bail profile refinement and pseudo-Voigt profile function using the JANA2006 software. In addition, a progressive Rietveld refinement in order to minimize the differences between the pattern observed and the calculated one with structural models was carried out to solve and quantify the framework and extra-framework structure (structural type and atomic positions) using JANA2006 software.

Figure 6:
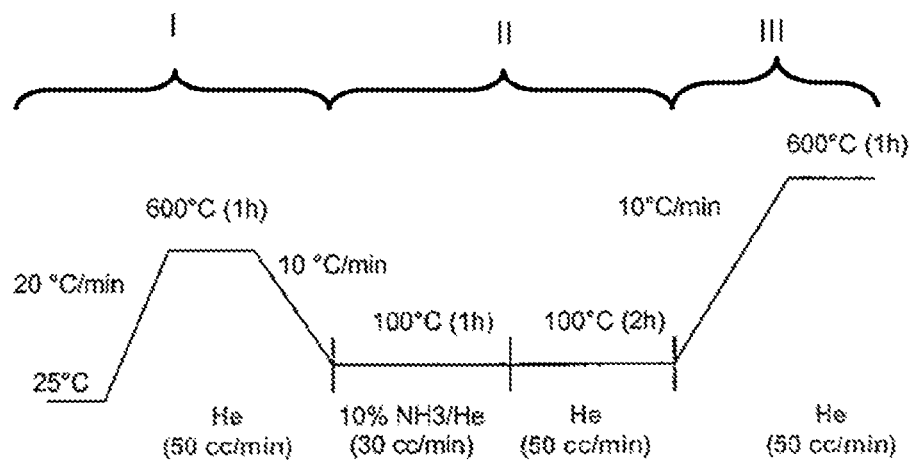
FIG. 6 shows an example of the settings of the temperature-programmed desorption (TPD) method.

Temperature Programmed Desorption (TPD) is the method of observing desorbed molecules from a surface when the surface temperature is increased. It has been performed by following the heating sequences I, II and III shows on FIG. 6, respectively corresponding to activation, saturation and analysis. In brief, in the first step (marked as I on FIG. 6), starting from room temperature (25° C.) under a flow of helium (rate 50 cc/min), the temperature has been gradually increased to 600° C. at a rate of 20° C./min. After 1 hour at 600° C., the solid acid sample is considered as being activated and the temperature Is then gradually decreased to 100° C. at a rate of 10° C./min. Then, in the second step (marked as II on FIG. 6) during 3 hours, the temperature is maintained at 100° C. and in the first 1 hour, 10% of ammonia ($NH_3$) is added to the helium flow (which is decreased to 30 cc/min). The surface of the solid acid is thus saturated with the molecules of ammonia that are going to be adsorbed onto the surface. The last 2 hours of the temperature threshold at 100° C., the initial flow of helium is reinstated. Then, in the third step (marked as III in FIG. 6) the temperature is increased again to 600° C. at a rate of 10° C./min in order to desorb the ammonia. The sample is maintained at 600° C. for an additional one hour. It is highlighted that the skilled person could use different parameters (time, temperature, flow rate, carrier gas) to perform the method. The measurement of the amount of ammonia using a thermal conductivity detector allows to recognize the different adsorption conditions of the ammonia onto the solid acid and allows for obtaining a description of the surface of the solid acid, such as the number of acid sites.

X-Ray Fluorescence Spectroscopy (XRF)

X-ray fluorescence (XRF) spectroscopy measurements have been taken by using an Orbis Micro-EDXRF spectrometer equipped with a Rh source (15 kV, 500 μA) and a silicon drift detector. XRF measurements were taken on the materials as such (non-dissolved). This was useful for determining the amount of $SiO_2$ and of $Al_2O_3$ and subsequently the Si/Al atomic ratio.

$N_2$ Sorption Measurements $N_2$ sorption analysis was used to determine the nitrogen adsorption/desorption isotherms using Micrometrics ASAP 2020 volumetric adsorption analyser. The samples were degassed at 350° C. under vacuum overnight before the measurement. From these measurements, the specific surface area of the solid acid catalyst has been determined.

The invention claimed is:

1. A process to perform a catalytic dehydration of one or more alcohols having at least two carbon atoms into one or more olefins, said process comprising the steps of:
    a) providing at least one fluidized bed reactor comprising at least two electrodes and a bed comprising particles;
    b) putting the particles of the bed in a fluidized state by passing upwardly through the said bed a fluid stream, to obtain a fluidized bed;
    c) heating the fluidized bed to a temperature ranging from 200° C. to 500° C. to conduct the catalytic dehydration of an alcohol-containing feedstock into one or more olefins, wherein the alcohol-containing feedstock comprises one or more alcohols having at least two carbon atoms; and
    d) optionally, recovering the one or more olefins;
    characterized in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm·cm to 500 Ohm·cm at 400° C.; wherein the catalytic composition comprises one or more solid acid catalysts; and in that the step c) of heating the fluidized bed is performed by passing an electric current through the fluidized bed.

2. The process according to claim 1 is characterized in that the electrically conductive particles of the bed comprise one or more selected from one or more metallic alloys, one or more non-metallic resistors, one or more metallic carbides, one or more metallic nitrides, one or more metallic phosphides, one or more carbon-containing particles, one or more superionic conductors, one or more phosphate electrolytes, and/or any mixture thereof.

3. The process according to claim 1 is characterized in that the electrically conductive particles of the bed comprise a mixture of a non-metallic resistor being silicon carbide and electrically conductive particles different from silicon carbide.

4. The process according to claim 3 is characterized in that the electrically conductive particles of the bed comprise from 10 wt. % to 99 wt. % of silicon carbide based on the total weight of the electrically conductive particles of the bed; and/or
the said electrically conductive particles different from silicon carbide are one or more carbon-containing particles.

5. The process according to claim 3 is characterized in that the said electrically conductive particles different from silicon carbide are one or more carbon-containing particles.

6. The process according to claim 1 is characterized in that the electrically conductive particles of the bed comprise one or more metallic alloys; and/or one or more superionic conductors.

7. The process according to claim 1 is characterized in that the electrically conductive particles of the bed comprise one or more superionic conductors are selected from $LiAlSiO_4$, $Li_{10}GeP_2S_{12}$, $Li_{3.6}Si_{0.6}P_{0.4}O_4$, sodium superionic conductors, or sodium beta alumina.

8. The process according to claim 1 is characterized in that the one or more alcohols having at least two carbon atoms are selected from ethanol, n-propanol, iso-propanol, n-butanol, sec-butanol, iso-butanol, tert-butanol, hexan-1-ol, hexan-2-ol, hexan-3-ol, 2-methylpentan-1-ol, 3-methylpentan-1-ol, 4-methylpentan-1-ol, 2-methylpentan-2-ol, 3-methylpentan-2-ol, 4-methylpentan-2-ol, 2-methylpentan-3-ol, 3-methylpentan-3-ol, 2,2-dimethylbutan-1-ol, 2-3-dimethylbutan-1-ol, 3,3-dimethylbutan-1-ol, 2,3-dimethylbutan-2-ol, 3,3-dimethylbutan-2-ol, 2-ethylbutan-1-ol or any combinations thereof.

9. The process according to claim 1 is characterized in that a step of pre-heating with a gaseous stream said fluidized bed reactor before conducting the catalytic dehydration of one or more alcohols having at least two carbon atoms into one or more olefins in the fluidized bed reactor; with preference, said gaseous stream is a stream of one or more inert gases selected among nitrogen, argon, helium, saturated hydrocarbons having up to 10 carbon atoms, or any combinations thereof and/or has a temperature comprised between 100° C. and 300° C.

10. The process according to claim 1 is characterized in that, wherein the at least one fluidized bed reactor provided in step a) comprises a heating zone and a reaction zone and wherein the fluid stream provided in step b) is provided to the heating zone, the step c) of heating the fluidized bed to a temperature ranging from 200° C. to 500° C. to conduct the endothermic catalytic dehydration of an alcohol-containing feedstock into one or more olefins, wherein the alcohol-containing feedstock comprises one or more alcohols having at least two carbon atoms, comprises the following sub steps:
heating the fluidized bed to a temperature ranging from 200° C. to 500° C. by passing an electric current through the heating zone of the at least one fluidized bed,
transporting the heated particles from the heating zone to the reaction zone,
in the reaction zone, putting the heated particles in a fluidized state by passing upwardly through the said bed of the reaction zone a fluid stream comprising an alcohol-containing feedstock, and optionally one or more inert gases and/or one or more diluent gases, to obtain a fluidized bed and to conduct the endothermic catalytic dehydration of an alcohol-containing feedstock into one or more olefins.

11. The process according to claim 1 is characterized in that the at least one fluidized bed reactor (18, 19, 37, 39) provided in step a) comprises a heating zone (27) and a reaction zone (29), and wherein the step c) of heating the fluidized bed (25) comprises the following sub-steps:
pre-heating the fluidized bed (25) to a temperature ranging from 100° C. to 300° C. by passing upwardly through the particles of the bed (25) a fluidizing stream being a gaseous stream having a temperature ranging from 100° C. to 300° C.;
heating the fluidized bed (25) to a temperature ranging from 200° C. to 500° C. by passing an electric current through the heating zone (27) of the at least one fluidized bed reactor (18, 19, 37, 39),
transporting the heated particles from the heating zone (27) to the reaction zone (29),
in the reaction zone (29), putting the heated particles in a fluidized state by passing upwardly through the said bed (25) of the reaction zone (29) a fluid stream comprising an alcohol-containing feedstock to obtain a fluidized bed (25) and to conduct the endothermic catalytic dehydration of one or more alcohols having at least two carbon atoms into one or more olefins,
optionally, recovering the particles from the reaction zone (29) and recycling them to the heating zone (27).

12. The process according to claim 1 is characterized in that the one or more solid acid catalysts have a surface area ranging between 50 $m^2$/g and 800 $m^2$/g as determined by $N_2$ sorption measurements and/or in that the content of the particles of the catalytic composition is ranging from 15 wt. % to 90 wt. % based on the total weight of the particles of the bed.

13. The process according to claim 1 is characterized in that the one or more solid acid catalysts are selected from one or more oxides, one or more mixed oxides, one or more phosphates, one or more zeolites, one or more silicoaluminophosphate molecular sieves or a combination thereof.

14. The process according to claim 1 is characterized in that the one or more solid acid catalysts are mixed with a binder.

15. The process according to claim 14 is characterized in that the binder is an inorganic material selected from one or more clays, silica, one or more metal silicates, one or more metal oxides, one or more gels or a combination thereof.

16. The process according to claim 1 is characterized in that said step (d) is carried out, and said process comprises a step (e) of oligomerizing one part of the one or more olefins recovered at step (d), said process further comprises a step (f) of providing one or more aromatic compounds and a step (g) of alkylating said one or more aromatic compounds with another part of the one or more olefins recovered at step (d), said step (g) being carried out concomitantly with said step (e).

17. Use of a bed (25) comprising particles in at least one fluidized bed reactor (18, 19, 37, 39) to perform a process of catalytic dehydration of one or more alcohols having at least two carbon atoms into olefins according to claim 1 the use is characterized in that at least 10 wt. % of the particles of the bed (25) based on the total weight of the particles of the bed are electrically conductive and have a resistivity ranging from 0.001 Ohm·cm to 500 Ohm·cm at 400° C.

* * * * *